United States Patent
Yoseph et al.

(10) Patent No.: US 11,466,071 B2
(45) Date of Patent: Oct. 11, 2022

(54) HLA CLASS I-RESTRICTED T CELL RECEPTORS AGAINST MUTATED RAS

(71) Applicant: The United States of America, as represented by the Secretary, Department of Health and Human Services, Bethesda, MD (US)

(72) Inventors: Rami Yoseph, Gaithersburg, MD (US); Yong-Chen Lu, Rockville, MD (US); Gal Cafri, Kibbutz Nir David (IL); Steven A. Rosenberg, Potomac, MD (US)

(73) Assignee: The United States of America, as represented by the Secretary, Department of Health and Human Services, Bethesda, MD (US)

(*) Notice: Subject to any disclaimer, the term of this patent is extended or adjusted under 35 U.S.C. 154(b) by 19 days.

(21) Appl. No.: 16/769,144

(22) PCT Filed: Dec. 3, 2018

(86) PCT No.: PCT/US2018/063581
§ 371 (c)(1),
(2) Date: Jun. 2, 2020

(87) PCT Pub. No.: WO2019/112941
PCT Pub. Date: Jun. 13, 2019

(65) Prior Publication Data
US 2021/0079058 A1   Mar. 18, 2021

Related U.S. Application Data

(60) Provisional application No. 62/594,244, filed on Dec. 4, 2017.

(51) Int. Cl.
| | | |
|---|---|---|
| C07K 14/725 | (2006.01) | |
| G01N 33/574 | (2006.01) | |
| A61K 38/00 | (2006.01) | |
| C12N 15/00 | (2006.01) | |

(52) U.S. Cl.
CPC ....... C07K 14/7051 (2013.01); G01N 33/574 (2013.01); A61K 38/00 (2013.01); C12N 15/00 (2013.01); C12N 2320/00 (2013.01)

(58) Field of Classification Search
None
See application file for complete search history.

(56) References Cited

U.S. PATENT DOCUMENTS

| 8,034,334 B2 | 10/2011 | Dudley et al. |
| 8,383,099 B2 | 2/2013 | Dudley et al. |
| 9,345,748 B2 * | 5/2016 | Morgan .................... A61P 1/04 |
| 2012/0244133 A1 | 9/2012 | Rosenberg et al. |
| 2021/0052642 A1 * | 2/2021 | Cafri .................... C12N 5/0639 |

FOREIGN PATENT DOCUMENTS

| WO | 2016/085904 A1 | 6/2016 |
| WO | 2017/048593 A1 | 3/2017 |
| WO | 2017/109109 A1 | 6/2017 |
| WO | 2017/112944 A1 | 6/2017 |

OTHER PUBLICATIONS

Cox et al., "Drugging the undruggable RAS: Mission possible?" *Nat Rev Drug Discov* 13(11): 828-851 (2014).
Dudley et al., "Generation of tumor-infiltrating lymphocyte cultures for use in adoptive transfer therapy for melanoma patients," *J. Immunother.*, 26(4):332-42 (2003).
International Bureau, International Search Report and Written Opinion in International Application No. PCT/US2018/063581, dated Feb. 25, 2019.
Riddell et al., "The use of anti-CD3 and anti-CD28 monoclonal antibodies to clone and expand human antigen-specific T cells," *J. Immunol. Methods*, 128(2):189-201 (1990).
Tran et al., "Cancer immunotherapy based on mutation-specific CD4+ T cells in a patient with epithelial cancer" and Supplementary Material, *Science*, 344(6184): 641-645 (2014).
Tran et al., "Immunogenicity of somatic mutations in human gastrointestinal cancers" and Supplementary Material, *Science*, 350(6266): 1387-1390 (2015).
Tran et al., "T-Cell Transfer Therapy Targeting Mutant KRAS in Cancer" and Supplementary Material, *N. Engl. J. Med.*, 375(23): 2255-2262 (2016).
Wang et al., "Identification of T-cell Receptors Targeting KRAS-Mutated Human Tumors," *Cancer Immunol. Res.*, 4(3): 204-214 (2016).
Wargo et al., "Recognition of NY-ESO-1 + tumor cells by engineered lymphocytes is enhanced by improved vector design and epigenetic modulation of tumor antigen expression," *Cancer Immunol. Immunother.*, 58(3): 383-394 (2009).

* cited by examiner

*Primary Examiner* — Nancy J Leith
(74) *Attorney, Agent, or Firm* — Leydig, Voit & Mayer, Ltd.

(57) ABSTRACT

Disclosed is an isolated or purified T cell receptor (TCR), wherein the TCR has antigenic specificity for a mutated RAS amino acid sequence presented by a human leukocyte antigen (HLA) Class I molecule. Related polypeptides and proteins, as well as related nucleic acids, recombinant expression vectors, host cells, populations of cells, and pharmaceutical compositions are also provided. Also disclosed are methods of detecting the presence of cancer in a mammal and methods of treating or preventing cancer in a mammal.

44 Claims, 6 Drawing Sheets
Specification includes a Sequence Listing.

HLA CLASS I-RESTRICTED T CELL RECEPTORS AGAINST MUTATED RAS

CROSS-REFERENCE TO RELATED APPLICATION

This patent application is the U.S. national stage of PCT/US2018/063581, filed Dec. 3, 2018, which claims the benefit of U.S. Provisional Patent Application No. 62/594,244, filed Dec. 4, 2017, each of which is incorporated by reference in its entirety herein.

STATEMENT REGARDING FEDERALLY SPONSORED RESEARCH AND DEVELOPMENT

This invention was made with Government support under project number BC010985 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 37,145 Byte ASCII (Text) file named "748582 ST25.txt" dated Jun. 1, 2020.

BACKGROUND OF THE INVENTION

Some cancers may have very limited treatment options, particularly when the cancer becomes metastatic and unresectable. Despite advances in treatments such as, for example, surgery, chemotherapy, and radiation therapy, the prognosis for many cancers, such as, for example, pancreatic, colorectal, lung, endometrial, ovarian, and prostate cancers, may be poor. Accordingly, there exists an unmet need for additional treatments for cancer.

BRIEF SUMMARY OF THE INVENTION

An embodiment of the invention provides an isolated or purified T-cell receptor (TCR) comprising the amino acid sequences of (i) SEQ ID NOs: 1-3, (ii) SEQ ID NOs: 4-6, or (iii) SEQ ID NOs: 1-6, wherein the TCR has antigenic specificity for a mutated human RAS amino acid sequence presented by a human leukocyte antigen (HLA) Class I molecule, and wherein the mutated human RAS amino acid sequence is a mutated human Kirsten rat sarcoma viral oncogene homolog (KRAS), a mutated human Harvey rat sarcoma viral oncogene homolog (HRAS), or a mutated human Neuroblastoma rat sarcoma viral oncogene homolog (NRAS) amino acid sequence.

Another embodiment of the invention provides an isolated or purified polypeptide comprising a functional portion of the inventive TCR, wherein the functional portion comprises the amino acid sequences of: (a) all of SEQ ID NOs: 1-3, (b) all of SEQ ID NOs: 4-6, or (c) all of SEQ ID NOs: 1-6.

Still another embodiment of the invention provides an isolated or purified protein comprising at least one of the inventive polypeptides.

Further embodiments of the invention provide nucleic acids, recombinant expression vectors, host cells, populations of cells, and pharmaceutical compositions relating to the inventive TCRs, polypeptides, and proteins.

Methods of detecting the presence of cancer in a mammal and methods of treating or preventing cancer in a mammal are further provided by embodiments of the invention.

DETAILED DESCRIPTION OF THE INVENTION

Figure 1A:
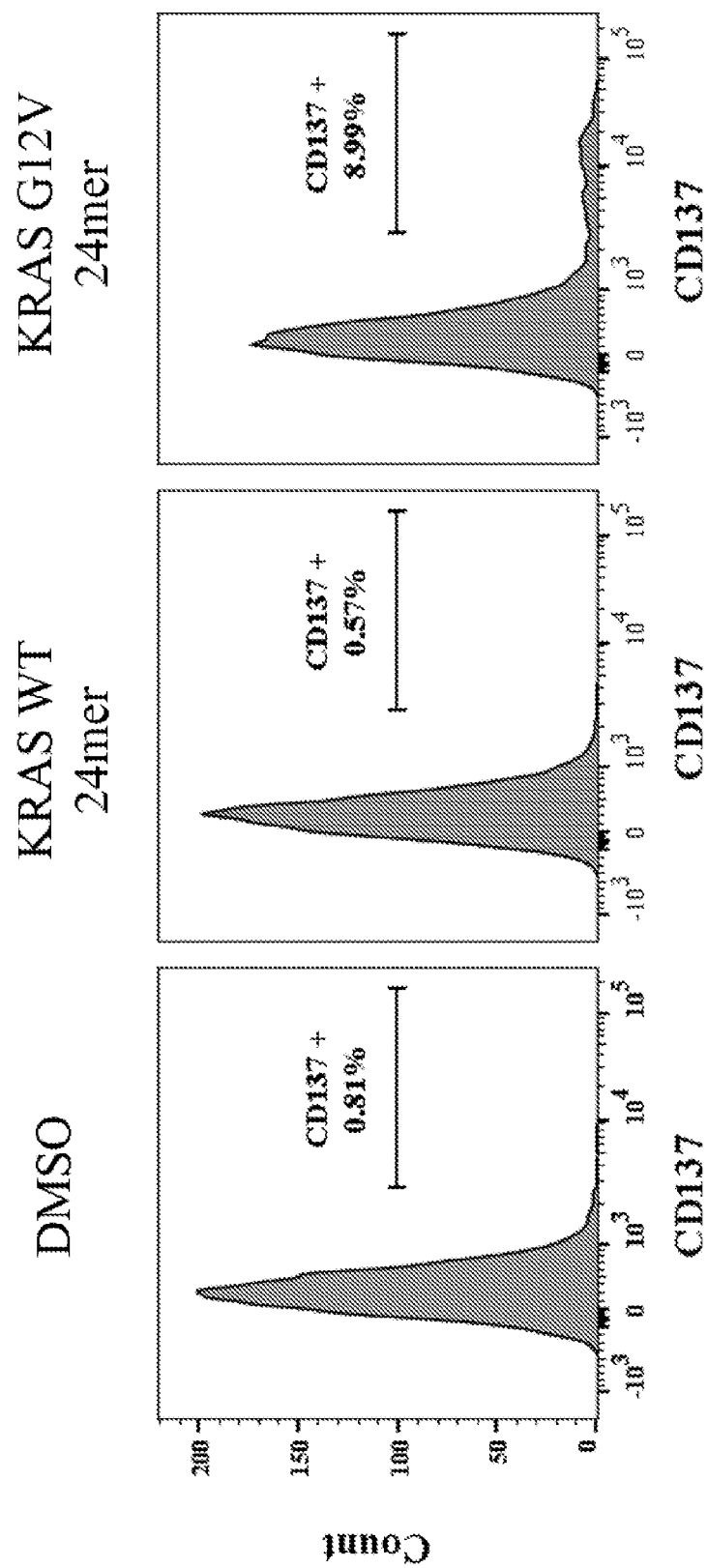
FIG. 1A depicts graphs illustrating CD137 expression by peripheral blood CD8+ T cells following co-culture with dimethyl sulfoxide (DMSO) or autologous DCs pulsed with the KRAS WT 24-mer peptide or the KRAS G12V 24-mer peptide. The numbers in the boxes indicate the percentages of T cells expressing CD137 in each co-culture condition.

RAS family proteins belong to the large family of small GTPases. Without being bound to a particular theory or mechanism, it is believed that, when mutated, RAS proteins may be involved in signal transduction early in the oncogenesis of many human cancers. A single amino acid substitution may activate the protein. The mutated RAS protein product may be constitutively activated. Mutated RAS proteins may be expressed in any of a variety of human cancers such as, for example, pancreatic (e.g., pancreatic carcinoma), colorectal, lung (e.g., lung adenocarcinoma), endometrial, ovarian (e.g., epithelial ovarian cancer), and prostate cancers. The human RAS family proteins include Kirsten rat sarcoma viral oncogene homolog (KRAS), Harvey rat sarcoma viral oncogene homolog (HRAS), and Neuroblastoma rat sarcoma viral oncogene homolog (NRAS).

KRAS is also referred to as GTPase KRas, V-Ki-Ras2 Kirsten rat sarcoma viral oncogene, or KRAS2. There are two transcript variants of KRAS: KRAS variant A and KRAS variant B. Wild-type (WT) KRAS variant A has the amino acid sequence of SEQ ID NO: 9. Wild-type (WT) KRAS variant B has the amino acid sequence of SEQ ID NO: 10. Hereinafter, references to "KRAS" (mutated or unmutated (WT)) refer to both variant A and variant B, unless specified otherwise. When activated, mutated KRAS binds to guanosine-5'-triphosphate (GTP) and converts GTP to guanosine 5'-diphosphate (GDP).

HRAS is another member of the RAS protein family. HRAS is also referred to as Harvey Rat Sarcoma Viral Oncoprotein, V-Ha-Ras Harvey Rat Sarcoma Viral Oncogene Homolog, or Ras Family Small GTP Binding Protein H-Ras. WT HRAS has the amino acid sequence of SEQ ID NO: 11.

NRAS is still another member of the RAS protein family. NRAS is also referred to as GTPase NRas, V-Ras Neuroblastoma RAS Viral Oncogene Homolog, or NRAS1. WT NRAS has the amino acid sequence of SEQ ID NO: 12.

An embodiment of the invention provides an isolated or purified TCR having antigenic specificity for a mutated human RAS amino acid sequence (hereinafter, "mutated RAS") presented by a human leukocyte antigen (HLA) Class I molecule, wherein the mutated human RAS amino acid sequence is a mutated human KRAS, a mutated human HRAS, or a mutated human NRAS amino acid sequence. Hereinafter, references to a "TCR" also refer to functional portions and functional variants of the TCR, unless specified otherwise.

The inventive TCR may have antigenic specificity for any mutated human RAS protein, polypeptide or peptide amino acid sequence. In an embodiment of the invention, the mutated human RAS amino acid sequence is a mutated human KRAS amino acid sequence, a mutated human HRAS amino acid sequence, or a mutated human NRAS amino acid sequence. The amino acid sequences of WT human KRAS, NRAS, and HRAS protein each have a length of 188-189 amino acid residues and have a high degree of identity to one another. For example, the amino acid sequence of the WT human NRAS protein is 86.8% identical to that of the WT human KRAS protein. Amino acid residues 1-86 of the WT human NRAS protein and the WT human KRAS protein are 100% identical. The amino acid sequence of the WT human HRAS protein is 86.3% identical to that of the WT human KRAS protein. Amino acid residues 1-94 of the WT human HRAS protein and the WT human KRAS protein are 100% identical. Hereinafter, references to "RAS" (mutated or unmutated (WT)) collectively refer to KRAS, HRAS, and NRAS, unless specified otherwise.

In an embodiment of the invention, the mutated human RAS amino acid sequence comprises a WT RAS amino acid sequence with a substitution of glycine at position 12, wherein position 12 is defined by reference to the WT RAS protein, respectively. The WT RAS protein may be any of WT KRAS protein (SEQ ID NO: 9 or 10), WT HRAS protein (SEQ ID NO: 11), or WT NRAS protein (SEQ ID NO: 12) because, as explained above, amino acid residues 1-86 of the WT human NRAS protein and the WT human KRAS protein are 100% identical, and amino acid residues 1-94 of the WT human HRAS protein and the WT human KRAS protein are 100% identical. Accordingly, the amino acid residue at position 12 of each of WT KRAS, WT HRAS, and WT NRAS protein is the same, namely, glycine.

The glycine at position 12 of the WT RAS amino acid sequence may be substituted with any amino acid residue other than glycine. In an embodiment of the invention, the substitution is a substitution of glycine at position 12 of the WT RAS amino acid sequence with valine. In this regard, embodiments of the invention provide TCRs with antigenic specificity for any WT RAS protein, polypeptide or peptide amino acid sequence with a G12V mutation.

Mutations and substitutions of RAS are defined herein by reference to the amino acid sequence of WT RAS protein. Thus, mutations and substitutions of RAS are described herein by reference to the amino acid residue present at a particular position in WT RAS protein, followed by the position number, followed by the amino acid residue with which that residue has been replaced in the particular mutation or substitution under discussion. A RAS amino acid sequence (e.g., a RAS peptide) may comprise fewer than all of the amino acid residues of the full-length, WT RAS protein. Accordingly, position 12 is defined herein by reference to the WT full-length RAS protein (namely, any one of SEQ ID NOs: 9-12) with the understanding that the actual position of the corresponding residue in a particular example of a RAS amino acid sequence may be different. When the positions are as defined by any one of SEQ ID NOs: 9-12, the term "G12" refers to the glycine normally present at position 12 of any one of SEQ ID NOs: 9-12, and "G12V" indicates that the glycine normally present at position 12 of any one of SEQ ID NOs: 9-12 is replaced by a valine. For example, when a particular example of a RAS amino acid sequence is, e.g., TEYKLVVVGA<u>G</u>GVGKSALTIQLI (SEQ ID NO: 28) (an exemplary WT KRAS peptide corresponding to contiguous amino acid residues 2 to 24 of SEQ ID NO: 9), "G12V" refers to a substitution of the underlined glycine in SEQ ID NO: 28 with valine, even though the actual position of the underlined glycine in SEQ ID NO: 28 is 11.

Examples of full-length RAS proteins with the G12V mutation are set forth in Table 1 below.

TABLE 1

| Mutated Full-Length RAS Protein | SEQ ID NO: |
| --- | --- |
| G12V KRAS variant A | 13 |
| G12V KRAS variant B | 14 |
| G12V HRAS | 15 |
| G12V NRAS | 16 |

In an embodiment of the invention, the TCR has antigenic specificity for a RAS peptide with the G12V mutation described above, wherein the mutated RAS peptide has any length. In an embodiment of the invention, the mutated RAS peptide has any length suitable for binding to any of the HLA Class I molecules described herein. For example, the TCR may have antigenic specificity for a RAS peptide with the G12V mutation, the RAS peptide having a length of about 9 to about 10 amino acid residues. The mutated RAS peptide may comprise any contiguous amino acid residues of mutated RAS protein which include the G12V mutation. In an embodiment of the invention, the TCR may have antigenic specificity for a RAS peptide with the G12V mutation, the mutated RAS peptide having a length of about 9 amino acid residues or about 10 amino acid residues. Examples of specific peptides, each with the G12V mutation, which may be recognized by the inventive G12V TCR are 9-mer VVGAVGVGK (SEQ ID NO: 29) and 10-mer VVVGAVGVGK.

In an embodiment of the invention, the inventive TCRs are able to recognize mutated RAS presented by an HLA Class I molecule. In this regard, the TCR may elicit an immune response upon binding to mutated RAS within the context of an HLA Class I molecule. The inventive TCRs may bind to the HLA Class I molecule in addition to mutated RAS.

In an embodiment of the invention, the HLA Class I molecule is an HLA-A molecule. The HLA-A molecule is a heterodimer of an α chain and β2 microglobulin. The HLA-A α chain may be encoded by an HLA-A gene. (β2 microglobulin binds non-covalently to the alpha1, alpha2 and alpha3 domains of the alpha chain to build the HLA-A complex. The HLA-A molecule may be any HLA-A molecule. In an embodiment of the invention, the HLA Class I molecule is an HLA-A11 molecule. The HLA-A11 molecule may be any HLA-A11 molecule. Examples of HLA-A11 molecules may include, but are not limited to, HLA-A*11: 01, HLA-A*11:02, HLA-A*11:03, or HLA-A*11:04. Preferably, the HLA Class I molecule is an HLA-A*11:01 molecule.

The TCRs of the invention may provide any one or more of a variety of advantages, including when expressed by cells used for adoptive cell transfer. Mutated RAS is expressed by cancer cells and is not expressed by normal, noncancerous cells. Without being bound to a particular theory or mechanism, it is believed that the inventive TCRs advantageously target the destruction of cancer cells while minimizing or eliminating the destruction of normal, non-cancerous cells, thereby reducing, for example, by minimizing or eliminating, toxicity. Moreover, the inventive TCRs may, advantageously, successfully treat or prevent mutated RAS-positive cancers that do not respond to other types of treatment such as, for example, chemotherapy, surgery, or radiation. The RAS$^{G12}$ mutations are among the most common hotspot mutations found in many cancer types. For example, the KRAS G12V mutation is expressed in about 27% and about 9% of patients with pancreatic and colorectal cancers, respectively. Moreover, RAS family members share the G12 hotspot mutation in different cancer types (e.g. NRAS in melanoma). Additionally, the inventive TCRs may provide highly avid recognition of mutated RAS, which may provide the ability to recognize unmanipulated tumor cells (e.g., tumor cells that have not been treated with interferon (IFN)-γ, transfected with a vector encoding one or both of mutated RAS and HLA-A*11:01, pulsed with a RAS peptide with the G12V mutation, or a combination thereof). Moreover, the HLA-A*11:01 allele is expressed in approximately 14% and approximately 9% of the Caucasian and Hispanic ethnicities, respectively. The HLA-A*11:01 allele is expressed by up to about 45% of the Asian ethnicity in the United States. Accordingly, the inventive TCRs may increase the number of immunotherapy-eligible cancer patients to include those patients that express the HLA-A*11:01 allele who may not be eligible for immunotherapy using TCRs that recognize RAS presented by other MHC molecules. Moreover, the inventive TCRs, polypeptides and proteins comprise human amino acid sequences, which may reduce the risk of rejection by the human immune system as compared to, e.g., TCRs, polypeptides and proteins comprising mouse amino acid sequences.

The phrase "antigenic specificity," as used herein, means that the TCR can specifically bind to and immunologically recognize mutated RAS with high avidity. For example, a TCR may be considered to have "antigenic specificity" for mutated RAS if about $1\times10^4$ to about $1\times10^5$ T cells expressing the TCR secrete at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, 20,000 pg/mL or more, or a range defined by any two of the foregoing values) of IFN-γ upon co-culture with (a) antigen-negative, HLA Class I molecule positive target cells pulsed with a low concentration of mutated RAS peptide (e.g., about 0.05 ng/mL to about 10 ng/mL, 1 ng/mL, 2 ng/mL, 5 ng/mL, 8 ng/mL, 10 ng/mL, or a range defined by any two of the foregoing values) or (b) antigen-negative, HLA Class I molecule positive target cells into which a nucleotide sequence encoding mutated RAS has been introduced such that the target cell expresses mutated RAS. Cells expressing the inventive TCRs may also secrete IFN-γ upon co-culture with antigen-negative, HLA Class I molecule positive target cells pulsed with higher concentrations of mutated RAS peptide. The HLA Class I molecule may be any of the HLA Class I molecules described herein (e.g., an HLA-A*11:01 molecule).

Alternatively or additionally, a TCR may be considered to have "antigenic specificity" for mutated RAS if T cells expressing the TCR secrete at least twice as much IFN-γ upon co-culture with (a) antigen-negative, HLA Class I molecule positive target cells pulsed with a low concentration of mutated RAS peptide or (b) antigen-negative, HLA Class I molecule positive target cells into which a nucleotide sequence encoding mutated RAS has been introduced such that the target cell expresses mutated RAS as compared to the amount of IFN-γ expressed by a negative control. The negative control may be, for example, (i) T cells expressing the TCR, co-cultured with (a) antigen-negative, HLA Class I molecule positive target cells pulsed with the same concentration of an irrelevant peptide (e.g., some other peptide with a different sequence from the mutated RAS peptide) or (b) antigen-negative, HLA Class I molecule positive target cells into which a nucleotide sequence encoding an irrelevant peptide has been introduced such that the target cell expresses the irrelevant peptide, or (ii) untransduced T cells (e.g., derived from PBMC, which do not express the TCR) co-cultured with (a) antigen-negative, HLA Class I molecule positive target cells pulsed with the same concentration of mutated RAS peptide or (b) antigen-negative, HLA Class I molecule positive target cells into which a nucleotide sequence encoding mutated RAS has been introduced such that the target cell expresses mutated RAS. The HLA Class I molecule expressed by the target cells of the negative control would be the same HLA Class I molecule expressed by the target cells that are co-cultured with the T cells being tested. The HLA Class I molecule may be any of the HLA Class I molecules described herein (e.g., an HLA-A*11:01 molecule). IFN-γ secretion may be measured by methods known in the art such as, for example, enzyme-linked immunosorbent assay (ELISA).

Alternatively or additionally, a TCR may be considered to have "antigenic specificity" for mutated RAS if at least twice as many of the numbers of T cells expressing the TCR secrete IFN-γ upon co-culture with (a) antigen-negative, HLA Class I molecule positive target cells pulsed with a low concentration of mutated RAS peptide or (b) antigen-negative, HLA Class I molecule positive target cells into which a nucleotide sequence encoding mutated RAS has been introduced such that the target cell expresses mutated RAS as compared to the numbers of negative control T cells that secrete IFN-γ. The HLA Class I molecule, concentration of peptide, and the negative control may be as described herein with respect to other aspects of the invention. The numbers of cells secreting IFN-γ may be measured by methods known in the art such as, for example, ELISPOT.

Alternatively or additionally, a TCR may be considered to have "antigenic specificity" for mutated RAS if T cells expressing the TCR upregulate expression of one or more T-cell activation markers as measured by, for example, flow cytometry after stimulation with target cells expressing mutated RAS. Examples of T-cell activation markers include 4-1BB, OX40, CD107a, CD69, and cytokines that are upregulated upon antigen stimulation (e.g., tumor necrosis factor (TNF), interleukin (IL)-2, etc.).

An embodiment of the invention provides a TCR comprising two polypeptides (i.e., polypeptide chains), such as an alpha (α) chain of a TCR, a beta ((β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for mutated RAS.

In an embodiment of the invention, the TCR comprises two polypeptide chains, each of which comprises a variable region comprising a complementarity determining region (CDR)1, a CDR2, and a CDR3 of a TCR. In an embodiment of the invention, the TCR comprises a first polypeptide chain comprising a CDR1 comprising the amino acid sequence of SEQ ID NO: 1 (CDR1 of α chain), a CDR2 comprising the amino acid sequence of SEQ ID NO: 2 (CDR2 of α chain), and a CDR3 comprising the amino acid sequence of SEQ ID NO: 3 (CDR3 of α chain), and a second polypeptide chain comprising a CDR1 comprising the amino acid sequence of SEQ ID NO: 4 (CDR1 of β chain), a CDR2 comprising the amino acid sequence of SEQ ID NO: 5 (CDR2 of β chain), and a CDR3 comprising the amino acid sequence of SEQ ID NO: 6 (CDR3 of (β chain). In this regard, the inventive TCR can comprise any one or more of the amino acid sequences selected from the group consisting of SEQ ID NOs:1-6. In an embodiment of the invention, the TCR comprises the amino acid sequences of: (a) all of SEQ ID NOs: 1-3, (b) all of SEQ ID NOs: 4-6, or (c) all of SEQ ID NOs: 1-6. In an especially preferred embodiment, the TCR comprises the amino acid sequences of all of SEQ ID NOs: 1-6.

In an embodiment of the invention, the TCR comprises an amino acid sequence of a variable region of a TCR comprising the CDRs set forth above. The TCR may comprise a human variable region, e.g., a human α chain variable region and a human β chain variable region. In this regard, the TCR can comprise the amino acid sequence of: SEQ ID NO: 7 (variable region of α chain); SEQ ID NO: 8 (variable region of β chain); or both of SEQ ID NOs: 7 and 8. Preferably, the TCR comprises the amino acid sequences of both of SEQ ID NOs: 7 and 8.

The inventive TCRs may further comprise an α chain constant region and a β chain constant region. The constant region may be derived from any suitable species such as, e.g., human or mouse. In an embodiment of the invention, the TCRs further comprise murine α and β chain constant regions or human α and β chain constant regions. As used herein, the term "murine" or "human," when referring to a TCR or any component of a TCR described herein (e.g., complementarity determining region (CDR), variable region, constant region, α chain, and/or (β chain), means a TCR (or component thereof) which is derived from a mouse or a human, respectively, i.e., a TCR (or component thereof) that originated from or was, at one time, expressed by a mouse T cell or a human T cell, respectively.

An embodiment of the invention provides a chimeric TCR comprising a human variable region and a murine constant region, wherein the TCR has antigenic specificity for a mutated human RAS amino acid sequence presented by an HLA Class I molecule. The murine constant region may provide any one or more advantages. For example, the murine constant region may diminish mispairing of the inventive TCR with the endogenous TCRs of the host cell into which the inventive TCR is introduced. Alternatively or additionally, the murine constant region may increase expression of the inventive TCR as compared to the same TCR with a human constant region. The chimeric TCR may comprise the amino acid sequence of SEQ ID NO: 19 (wild-type (WT) murine α chain constant region), SEQ ID NO: 20 (WT murine β chain constant region), or both SEQ ID NOs: 19 and 20. Preferably, the inventive TCR comprises the amino acid sequences of both of SEQ ID NOs: 19 and 20. The chimeric TCR may comprise any of the murine constant regions described herein in combination with any of the CDR regions as described herein with respect to other aspects of the invention. In this regard, the TCR may comprise the amino acid sequences of: (a) all of SEQ ID NOs: 1-3 and 19; (b) all of SEQ ID NOs: 4-6 and 20; or (c) all of SEQ ID NOs: 1-6 and 19-20. In another embodiment of the invention, the chimeric TCR may comprise any of the murine constant regions described herein in combination with any of the variable regions described herein with respect to other aspects of the invention. In this regard, the TCR may comprise the amino acid sequences of: (i) both of SEQ ID NOs: 7 and 19; (ii) both of SEQ ID NOs: 8 and 20; or (iii) all of SEQ ID NOs: 7-8 and 19-20.

In another embodiment of the invention, the TCR comprises the amino acid sequence(s) of: SEQ ID NO: 23 (α chain with WT murine constant region), SEQ ID NO: 24 (l chain with WT murine constant region), or both of SEQ ID NOs: 23-24.

In an embodiment of the invention, the TCR comprises a substituted constant region. In this regard, the TCR may comprise the amino acid sequence of any of the TCRs described herein with one, two, three, or four amino acid substitution(s) in the constant region of one or both of the α and β chain. Preferably, the TCR comprises a murine constant region with one, two, three, or four amino acid substitution(s) in the murine constant region of one or both of the α and β chains. In an especially preferred embodiment, the TCR comprises a murine constant region with one, two, three, or four amino acid substitution(s) in the murine constant region of the α chain and one amino acid substitution in the murine constant region of the β chain. In some embodiments, the TCRs comprising the substituted constant region advantageously provide one or more of increased recognition of mutated RAS$^+$ targets, increased expression by a host cell, diminished mispairing with endogenous TCRs, and increased anti-tumor activity as compared to the parent TCR comprising an unsubstituted (wild-type) constant region. In general, the substituted amino acid sequences of the murine constant regions of the TCR α and β chains, SEQ ID NOs: 17 and 18, respectively, correspond with all or portions of the unsubstituted murine constant region amino acid sequences SEQ ID NOs: 19 and 20, respectively, with SEQ ID NO: 17 having one, two, three, or four amino acid substitution(s) when compared to SEQ ID NO: 19 and SEQ ID NO: 18 having one amino acid substitution when compared to SEQ ID NO: 20. In this regard, an embodiment of the invention provides a TCR comprising the amino acid sequences of (a) SEQ ID NO: 17 (constant region of α chain), wherein (i) X at position 48 is Thr or Cys; (ii) X at position 112 is Ser, Ala, Val, Leu, Ile, Pro, Phe, Met, or Trp; (iii) X at position 114 is Met, Ala, Val, Leu, Ile, Pro, Phe, or Trp; and (iv) X at position 115 is Gly, Ala, Val, Leu, Ile, Pro, Phe, Met, or Trp; (b) SEQ ID NO: 18 (constant region of β chain), wherein X at position 57 is Ser or Cys; or (c) both of SEQ ID NOs: 17 and 18. In an embodiment of the invention, the TCR comprising SEQ ID NO: 17 does not comprise SEQ ID NO: 19 (unsubstituted murine constant region of α chain). In an embodiment of the invention, the TCR comprising SEQ ID NO: 18 does not comprise SEQ ID NO: 20 (unsubstituted murine constant region of β chain).

In an embodiment of the invention, the TCR comprises an α chain comprising a variable region and a constant region and a β chain comprising a variable region and a constant region. In this regard, the TCR may comprise (a) an α chain comprising the amino acid sequence of SEQ ID NO: 21, wherein: (i) X at position 185 of SEQ ID NO: 21 is Thr or Cys; (ii) X at position 249 of SEQ ID NO: 21 is Ser, Ala, Val, Leu, Ile, Pro, Phe, Met, or Trp; (iii) X at position 251 of SEQ ID NO: 21 is Met, Ala, Val, Leu, Ile, Pro, Phe, or Trp; and (iv) X at position 252 of SEQ ID NO: 21 is Gly, Ala, Val, Leu, Ile, Pro, Phe, Met, or Trp; (b) a β chain comprising the amino acid sequence of SEQ ID NO: 22, wherein X at position 190 of SEQ ID NO: 22 is Ser or Cys; or (c) both (a) and (b). In an embodiment of the invention, the TCR comprising SEQ ID NO: 21 does not comprise SEQ ID NO: 23 (unsubstituted α chain). In an embodiment of the invention, the TCR comprising SEQ ID NO: 22 does not comprise SEQ ID NO: 24 (unsubstituted (β chain).

In an embodiment of the invention, the substituted constant region includes cysteine substitutions in the constant region of one or both of the α and β chains to provide a cysteine-substituted TCR. Opposing cysteines in the α and the β chains provide a disulfide bond that links the constant regions of the α and the β chains of the substituted TCR to one another and which is not present in a TCR comprising the unsubstituted murine constant regions. In this regard, the TCR may be a cysteine-substituted TCR in which one or both of the native Thr at position 48 (Thr48) of SEQ ID NO: 19 and the native Ser at position 57 (Ser57) of SEQ ID NO: 20 may be substituted with Cys. Preferably, both of the native Thr48 of SEQ ID NO: 19 and the native Ser57 of SEQ ID NO: 20 are substituted with Cys. Examples of cysteine-substituted TCR constant regions sequences are set forth in Table 2. In an embodiment of the invention, the cysteine-substituted TCR comprises (i) SEQ ID NO: 17, (ii) SEQ ID NO: 18, or (iii) both of SEQ ID NOs: 17 and 18, wherein both of SEQ ID NOs: 17 and 18 are as defined in Table 2. The cysteine-substituted TCRs of the invention may include the substituted constant region in addition to any of the CDRs or variable regions described herein.

In an embodiment of the invention, the cysteine-substituted, chimeric TCR comprises a full length alpha chain and a full-length beta chain. Examples of cysteine-substituted, chimeric TCR alpha chain and beta chain sequences are set forth in Table 2. In an embodiment of the invention, the TCR comprises (i) SEQ ID NO: 21, (ii) SEQ ID NO: 22, or (iii) both of SEQ ID NO: 21 and 22, wherein SEQ ID NOs: 21-22 are as defined in Table 2.

TABLE 2

| SEQ ID NO: | Definitions of "X" |
| --- | --- |
| SEQ ID NO: 17 (constant region α chain) | X at position 48 is Cys, X at position 112 is Ser, X at position 114 is Met, and X at position 115 is Gly. |
| SEQ ID NO: 18 (constant region β chain) | X at position 57 is Cys |
| SEQ ID NO: 21 (α chain) | X at position 185 is Cys, X at position 249 is Ser, X at position 251 is Met, and X at position 252 is Gly. |
| SEQ ID NO: 22 (β chain) | X at position 190 is Cys |

In an embodiment of the invention, the substituted amino acid sequence includes substitutions of one, two, or three amino acids in the transmembrane (TM) domain of the constant region of one or both of the α and β chains with a hydrophobic amino acid to provide a hydrophobic amino acid-substituted TCR (also referred to herein as an "LVL-modified TCR"). The hydrophobic amino acid substitution(s) in the TM domain of the TCR may increase the hydrophobicity of the TM domain of the TCR as compared to a TCR that lacks the hydrophobic amino acid substitution(s) in the TM domain. In this regard, the TCR is an LVL-modified TCR in which one, two, or three of the native Ser112, Met114, and Gly115 of SEQ ID NO: 19 may, independently, be substituted with Ala, Val, Leu, Ile, Pro, Phe, Met, or Trp; preferably with Leu, Ile, or Val. Preferably, all three of the native Ser112, Met114, and Gly115 of SEQ ID NO: 19 may, independently, be substituted with Ala, Val, Leu, Ile, Pro, Phe, Met, or Trp; preferably with Leu, Ile, or Val. In an embodiment of the invention, the LVL-modified TCR comprises (i) SEQ ID NO: 17, (ii) SEQ ID NO: 18, or (iii) both of SEQ ID NOs: 17 and 18, wherein both of SEQ ID NOs: 17 and 18 are as defined in Table 3. The LVL-modified TCRs of the invention may include the substituted constant region in addition to any of the CDRs or variable regions described herein.

In an embodiment of the invention, the LVL-modified TCR comprises a full length alpha chain and a full-length beta chain. Examples of LVL-modified TCR alpha chain and beta chain sequences are set forth in Table 3. In an embodiment of the invention, the LVL-modified TCR comprises (i) SEQ ID NO: 21, (ii) SEQ ID NO: 22, or (iii) both of SEQ ID NO: 21 and 22, wherein SEQ ID NOs: 21-22 are as defined in Table 3.

TABLE 3

| SEQ ID NO: | Definitions of "X" |
| --- | --- |
| SEQ ID NO: 17 (constant region α chain) | X at position 48 is Thr; X at position 112 is Ser, Ala, Val, Leu, Ile, Pro, Phe, Met, or Trp; preferably wherein X at position 112 is Leu, Ile, or Val; especially preferably wherein X at position 112 is Leu; X at position 114 is Met, Ala, Val, Leu, Ile, Pro, Phe, or Trp; preferably wherein X at position 114 is Leu, Ile, or Val; |

TABLE 3-continued

| SEQ ID NO: | Definitions of "X" |
|---|---|
| | especially preferably wherein X at position 114 is Ile; and X at position 115 is Gly, Ala, Val, Leu, Ile, Pro, Phe, Met, or Trp; preferably wherein X at position 115 is Leu, Ile, or Val; especially preferably wherein X at position 115 is Val; Wherein SEQ ID NO: 17 does not comprise SEQ ID NO: 19 (unsubstituted constant region of alpha chain) |
| SEQ ID NO: 18 (constant region β chain) | X at position 57 is Ser |
| SEQ ID NO: 21 (α chain) | X at position 185 is Thr; X at position 249 is Ser, Ala, Val, Leu, Ile, Pro, Phe, Met, or Trp; preferably wherein X at position 243 is Leu, Ile, or Val; especially preferably wherein X at position 243 is Leu; X at position 251 is Met, Ala, Val, Leu, Ile, Pro, Phe, or Trp; preferably wherein X at position 245 is Leu, Ile, or Val; especially preferably wherein X at position 245 is Ile; and X at position 252 is Gly, Ala, Val, Leu, Ile, Pro, Phe, Met, or Trp; preferably wherein X at position 246 is Leu, Ile, or Val; especially preferably wherein X at position 246 is Val, Wherein SEQ ID NO: 21 does not comprise SEQ ID NO: 23 (unsubstituted alpha chain) |
| SEQ ID NO: 22 (β chain) | X at position 190 is Ser |

In an embodiment of the invention, the substituted amino acid sequence includes the cysteine substitutions in the constant region of one or both of the α and β chains in combination with the substitution(s) of one, two, or three amino acids in the transmembrane (TM) domain of the constant region of one or both of the α and β chains with a hydrophobic amino acid (also referred to herein as "cysteine-substituted, LVL-modified TCR"). In this regard, the TCR is a cysteine-substituted, LVL-modified, chimeric TCR in which the native Thr48 of SEQ ID NO: 19 is substituted with Cys; one, two, or three of the native Ser112, Met114, and Gly115 of SEQ ID NO: 19 are, independently, substituted with Ala, Val, Leu, Ile, Pro, Phe, Met, or Trp; preferably with Leu, Ile, or Val; and the native Ser57 of SEQ ID NO: 20 is substituted with Cys. Preferably, all three of the native Ser112, Met114, and Gly115 of SEQ ID NO: 19 may, independently, be substituted with Ala, Val, Leu, Ile, Pro, Phe, Met, or Trp; preferably with Leu, Ile, or Val. In an embodiment of the invention, the cysteine-substituted, LVL-modified TCR comprises (i) SEQ ID NO: 17, (ii) SEQ ID NO: 18, or (iii) both of SEQ ID NOs: 17 and 18, wherein both of SEQ ID NOs: 17 and 18 are as defined in Table 4. The cysteine-substituted, LVL-modified TCRs of the invention may include the substituted constant region in addition to any of the CDRs or variable regions described herein.

In an embodiment, the cysteine-substituted, LVL-modified TCR comprises a full-length alpha chain and a full-length beta chain. In an embodiment of the invention, the cysteine-substituted, LVL-modified TCR comprises (i) SEQ ID NO: 21, (ii) SEQ ID NO: 22, or (iii) both of SEQ ID NO: 21 and 22, wherein SEQ ID NOs: 21-22 are as defined in Table 4.

TABLE 4

| SEQ ID NO: | Definitions of "X" |
|---|---|
| SEQ ID NO: 17 (constant region α chain) | X at position 48 is Cys; X at position 112 is Ser, Ala, Val, Leu, Ile, Pro, Phe, Met, or Trp; preferably wherein X at position 112 is Leu, Ile, or Val; especially preferably wherein X at position 112 is Leu; X at position 114 is Met, Ala, Val, Leu, Ile, Pro, Phe, or Trp; preferably wherein X at position 114 is Leu, Ile, or Val; especially preferably wherein X at position 114 is Ile; and X at position 115 is Gly, Ala, Val, Leu, Ile, Pro, Phe, Met, or Trp; preferably wherein X at position 115 is Leu, Ile, or Val; and especially preferably wherein X at position 115 is Val, wherein SEQ ID NO: 17 does not simultaneously comprise all of Ser at position 112, Met at position 114, and Gly at position 115. |
| SEQ ID NO: 18 (constant region β chain) | X at position 57 is Cys |
| SEQ ID NO: 21 (α chain) | X at position 185 is Cys; X at position 249 is Ser, Ala, Val, Leu, Ile, Pro, Phe, Met, or Trp; preferably wherein X at position 243 is Leu, Ile, or Val; especially preferably wherein X at position 243 is Leu; X at position 251 is Met, Ala, Val, Leu, Ile, Pro, Phe, or Trp; preferably wherein X at position 245 is Leu, Ile, or Val; especially preferably wherein X at position 245 is Ile; and X at position 252 is Gly, Ala, Val, Leu, Ile, Pro, Phe, Met, or Trp; preferably wherein X at position 246 is Leu, Ile, or Val; and especially preferably wherein X at position 246 is Val, wherein SEQ ID NO: 21 does not simultaneously comprise all of Ser at position 249, Met at position 251, and Gly at position 252. |

TABLE 4-continued

| SEQ ID NO: | Definitions of "X" |
|---|---|
| SEQ ID NO: 22 (β chain) | X at position 190 is Cys |

Also provided by an embodiment of the invention is a polypeptide comprising a functional portion of any of the TCRs described herein. The term "polypeptide," as used herein, includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to mutated RAS. The term "functional portion," when used in reference to a TCR, refers to any part or fragment of the TCR of the invention, which part or fragment retains the biological activity of the TCR of which it is a part (the parent TCR). Functional portions encompass, for example, those parts of a TCR that retain the ability to specifically bind to mutated RAS (e.g., within the context of an HLA-A*11:01 molecule), or detect, treat, or prevent cancer, to a similar extent, the same extent, or to a higher extent, as the parent TCR. In reference to the parent TCR, the functional portion can comprise, for instance, about 10%, about 25%, about 30%, about 50%, about 70%, about 80%, about 90%, about 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to mutated RAS; and/or having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one or more of the CDR1, CDR2, and CDR3 of the variable region(s) of the α chain and/or β chain of a TCR of the invention. In an embodiment of the invention, the polypeptide can comprise the amino acid sequence of SEQ ID NO: 1 (CDR1 of α chain), SEQ ID NO: 2 (CDR2 of α chain), SEQ ID NO: 3 (CDR3 of α chain), SEQ ID NO: 4 (CDR1 of β chain), SEQ ID NO: 5 (CDR2 of (β chain), SEQ ID NO: 6 (CDR3 of (3 chain), or a combination thereof.

In this regard, the inventive polypeptide can comprise any one or more of the amino acid sequences selected from the group consisting of SEQ ID NOs: 1-6. In an embodiment of the invention, the TCR comprises the amino acid sequences of: (a) all of SEQ ID NOs: 1-3, (b) all of SEQ ID NOs: 4-6, or (c) all of SEQ ID NOs: 1-6. In a preferred embodiment, the polypeptide comprises the amino acid sequences of all of SEQ ID NOs: 1-6.

In an embodiment of the invention, the inventive polypeptide can comprise, for instance, the variable region of the inventive TCR comprising a combination of the CDR regions set forth above. In this regard, the polypeptide can comprise the amino acid sequence of (i) SEQ ID NO: 7 (variable region of α chain), (ii) SEQ ID NO: 8 (variable region of (3 chain), or (iii) both of SEQ ID NOs: 7 and 8.

Preferably, the polypeptide comprises the amino acid sequences of both of SEQ ID NOs: 7 and 8.

In an embodiment of the invention, the inventive polypeptide can further comprise the constant region of the inventive TCR set forth above. In this regard, the polypeptide can further comprise the amino acid sequence of SEQ ID NO: 19 (WT murine constant region of α chain), SEQ ID NO: 20 (WT murine constant region of β chain), SEQ ID NO: 17, (substituted murine constant region of α chain), SEQ ID NO: 18 (substituted murine constant region of β chain), both SEQ ID NOs: 19 and 20, or both SEQ ID NOs: 17 and 18. Preferably, the polypeptide further comprises the amino acid sequences of both of SEQ ID NOs: 19 and 20 or both of SEQ ID NO: 17 and 18 in combination with any of the CDR regions or variable regions described herein with respect to other aspects of the invention.

In an embodiment of the invention, the polypeptide comprises: (a) the amino acid sequence of SEQ ID NO: 17, wherein: (i) X at position 48 of SEQ ID NO: 17 is Thr or Cys; (ii) X at position 112 of SEQ ID NO: 17 is Ser, Ala, Val, Leu, Ile, Pro, Phe, Met, or Trp; (iii) X at position 114 of SEQ ID NO: 17 is Met, Ala, Val, Leu, Ile, Pro, Phe, or Trp; and (iv) X at position 115 of SEQ ID NO: 17 is Gly, Ala, Val, Leu, Ile, Pro, Phe, Met, or Trp; (b) the amino acid sequence of SEQ ID NO: 18, wherein X at position 57 of SEQ ID NO: 18 is Ser or Cys; or (c) both (a) and (b). In an embodiment of the invention, one or both of SEQ ID NOs: 17 and 18 of the polypeptide are as defined in any one of Tables 2-4.

In an embodiment of the invention, the inventive polypeptide can comprise the entire length of an α or β chain of the TCR described herein. In this regard, the inventive polypeptide can comprise the amino acid sequence of SEQ ID NO: 21, SEQ ID NO: 22, SEQ ID NO: 23, SEQ ID NO: 24, both of SEQ ID NOs: 21 and 22, or both of SEQ ID NOs: 23 and 24. Preferably, the polypeptide comprises the amino acid sequences of both of SEQ ID NOs: 21 and 22 or both of SEQ ID NOs: 23 and 24.

In an embodiment of the invention, the polypeptide comprises: (a) the amino acid sequence of SEQ ID NO: 21, wherein: (i) X at position 185 of SEQ ID NO: 21 is Thr or Cys; (ii) X at position 249 of SEQ ID NO: 21 is Ser, Ala, Val, Leu, Ile, Pro, Phe, Met, or Trp; (iii) X at position 251 of SEQ ID NO: 21 is Met, Ala, Val, Leu, Ile, Pro, Phe, or Trp; and (iv) X at position 252 of SEQ ID NO: 21 is Gly, Ala, Val, Leu, Ile, Pro, Phe, Met, or Trp; (b) the amino acid sequence of SEQ ID NO: 22, wherein X at position 190 of SEQ ID NO: 22 is Ser or Cys; or (c) both (a) and (b). In an embodiment of the invention, any one or more of SEQ ID NOs: 21-22 of the polypeptide are as defined in any one of Tables 2-4.

An embodiment of the invention further provides a protein comprising at least one of the polypeptides described herein. By "protein" is meant a molecule comprising one or more polypeptide chains.

In an embodiment, the protein of the invention can comprise a first polypeptide chain comprising the amino acid sequences of SEQ ID NOs: 1-3 and a second polypeptide chain comprising the amino acid sequence of SEQ ID NOs: 4-6.

In another embodiment of the invention, the protein may comprise a first polypeptide chain comprising the amino acid sequences of SEQ ID NO: 7 and a second polypeptide chain comprising the amino acid sequences of SEQ ID NO: 8.

The inventive protein may further comprise any of the constant regions described herein with respect to other aspects of the invention. In this regard, in an embodiment of the invention, the first polypeptide chain may further comprise the amino acid sequence of SEQ ID NO: 17 and the second polypeptide chain may further comprise the amino acid sequence of SEQ ID NO: 18. In an embodiment of the invention, the first polypeptide chain may further comprise the amino acid sequence of SEQ ID NO: 19 and the second polypeptide chain may further comprise the amino acid sequence of SEQ ID NO: 20.

In an embodiment of the invention, the protein comprises: (a) a first polypeptide chain comprising the amino acid sequence of SEQ ID NO: 17, wherein: (i) X at position 48 of SEQ ID NO: 17 is Thr or Cys; (ii) X at position 112 of SEQ ID NO: 17 is Ser, Ala, Val, Leu, Ile, Pro, Phe, Met, or Trp; (iii) X at position 114 of SEQ ID NO: 17 is Met, Ala, Val, Leu, Ile, Pro, Phe, or Trp; and (iv) X at position 115 of SEQ ID NO: 17 is Gly, Ala, Val, Leu, Ile, Pro, Phe, Met, or Trp; (b) a second polypeptide chain comprising the amino acid sequence of SEQ ID NO: 18, wherein X at position 57 of SEQ ID NO: 18 is Ser or Cys; or (c) both (a) and (b). In an embodiment of the invention, one or both of SEQ ID NOs: 17 and 18 of the protein are as defined in any one of Tables 2-4.

Alternatively or additionally, the protein of an embodiment of the invention can comprise (a) a first polypeptide chain comprising the amino acid sequence of SEQ ID NO: 21, wherein: (i) X at position 185 of SEQ ID NO: 21 is Thr or Cys; (ii) X at position 249 of SEQ ID NO: 21 is Ser, Ala, Val, Leu, Ile, Pro, Phe, Met, or Trp; (iii) X at position 251 of SEQ ID NO: 21 is Met, Ala, Val, Leu, Ile, Pro, Phe, or Trp; and (iv) X at position 252 of SEQ ID NO: 21 is Gly, Ala, Val, Leu, Ile, Pro, Phe, Met, or Trp; (b) a second polypeptide chain comprising the amino acid sequence of SEQ ID NO: 22, wherein X at position 190 of SEQ ID NO: 22 is Ser or Cys; or (c) both (a) and (b). In an embodiment of the invention, the protein may comprise a first polypeptide chain comprising the amino acid sequence of SEQ ID NO: 23 and a second polypeptide chain comprising the amino acid sequence of SEQ ID NO: 24. In an embodiment of the invention, one or both of SEQ ID NOs: 21-22 are as defined in any one of Tables 2-4.

The protein of the invention can be a TCR. Alternatively, if, for example, the protein comprises a single polypeptide chain comprising the amino acid sequences of both SEQ ID NOs: 21 and 22, both SEQ ID NOs: 23 and 24, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, an embodiment of the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

In some embodiments of the invention, the TCRs, polypeptides, and proteins of the invention may be expressed as a single protein comprising a linker peptide linking the α chain and the β chain. In this regard, the TCRs, polypeptides, and proteins of the invention may further comprise a linker peptide. The linker peptide may advantageously facilitate the expression of a recombinant TCR, polypeptide, and/or protein in a host cell. The linker peptide may comprise any suitable amino acid sequence. For example, the linker peptide may be a furin-SGSG-P2A linker comprising the amino acid sequence of SEQ ID NO:25. Upon expression of the construct including the linker peptide by a host cell, the linker peptide may be cleaved, resulting in separated α and β chains. In an embodiment of the invention, the TCR, polypeptide, or protein may comprise an amino acid sequence comprising a full-length α chain, a full-length β chain, and a linker peptide positioned between the α and β chains.

The protein of the invention can be a recombinant antibody, or an antigen binding portion thereof, comprising at least one of the inventive polypeptides described herein. As used herein, "recombinant antibody" refers to a recombinant (e.g., genetically engineered) protein comprising at least one of the polypeptides of the invention and a polypeptide chain of an antibody, or an antigen binding portion thereof. The polypeptide of an antibody, or antigen binding portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or an antigen binding portion thereof, can exist as a separate polypeptide of the recombinant antibody. Alternatively, the polypeptide chain of an antibody, or an antigen binding portion thereof, can exist as a polypeptide, which is expressed in frame (in tandem) with the polypeptide of the invention. The polypeptide of an antibody, or an antigen binding portion thereof, can be a polypeptide of any antibody or any antibody fragment, including any of the antibodies and antibody fragments described herein.

Included in the scope of the invention are functional variants of the inventive TCRs, polypeptides, or proteins described herein. The term "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to mutated RAS for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, about 50%, about 75%, about 80%, about 90%, about 95%, about 96%, about 97%, about 98%, about 99% or more identical in amino acid sequence to the parent TCR, polypeptide, or protein, respectively.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the TCR, polypeptide, or protein, e.g., other amino acids, do not materially change the biological activity of the TCR, polypeptide, or protein. In this regard, the inventive TCR, polypeptide, or protein can, for example, consist essentially of the amino acid sequence of SEQ ID NO: 21, SEQ ID NO: 22, SEQ ID NO: 23, SEQ ID NO: 24, both of SEQ ID NOs: 21-22 or both of SEQ ID NO: 23-24. Also, for instance, the inventive TCRs, polypeptides, or proteins can consist essentially of the amino acid sequence(s) of (i) SEQ ID NO: 7, (ii) SEQ ID NO: 8, or (iii) both of SEQ ID NOs: 7 and 8. Furthermore, the inventive TCRs, polypeptides, or proteins can consist essentially of the amino acid sequences of (a) any one or more of SEQ ID NOs: 1-6; (b) all of SEQ ID NOs: 1-3; (c) all of SEQ ID NO: 4-6; or (d) all of SEQ ID NOs: 1-6.

The TCRs, polypeptides, and proteins of the invention can be of any length, i.e., can comprise any number of amino acids, provided that the TCRs, polypeptides, or proteins retain their biological activity, e.g., the ability to specifically bind to mutated RAS; detect cancer in a mammal; or treat or prevent cancer in a mammal, etc. For example, the polypeptide can be in the range of from about 50 to about 5000 amino acids long, such as about 50, about 70, about 75, about 100, about 125, about 150, about 175, about 200, about 300, about 400, about 500, about 600, about 700, about 800, about 900, about 1000 or more amino acids in length. In this regard, the polypeptides of the invention also include oligopeptides.

The TCRs, polypeptides, and proteins of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α, γ-diaminobutyric acid, α,β-diaminopropionic acid, homophenylalanine, and α-tert-butylglycine.

The TCRs, polypeptides, and proteins of the invention can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention can be obtained by methods known in the art such as, for example, de novo synthesis. Also, polypeptides and proteins can be recombinantly produced using the nucleic acids described herein using standard recombinant methods. See, for instance, Green and Sambrook, *Molecular Cloning: A Laboratory Manual*, 4$^{th}$ ed., Cold Spring Harbor Press, Cold Spring Harbor, N.Y. (2012). Alternatively, the TCRs, polypeptides, and/or proteins described herein can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs, polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art.

An embodiment of the invention provides a nucleic acid comprising a nucleotide sequence encoding any of the TCRs, polypeptides, or proteins described herein. "Nucleic acid," as used herein, includes "polynucleotide," "oligonucleotide," and "nucleic acid molecule," and generally means a polymer of DNA or RNA, which can be single-stranded or double-stranded, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green and Sambrook et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs, polypeptides, or proteins described herein. In an embodiment of the invention, the nucleic acid may comprise the nucleotide sequences of any one of SEQ ID NOs: 31-32 (Table 5). In an embodiment of the invention, the nucleic acid comprises the nucleotide sequences of both of SEQ ID NOs: 31-32.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%,

TABLE 5

| TCR ID | TCR chain | Nucleotide sequence |
|---|---|---|
| RAS$^{G12V}$-HLA-A*11:01 | Alpha (TRAV14/DV4*02) | SEQ ID NO: 31<br>atgcatctgagctccctgctgaaggtggtgacagccagcctgtggctgggaccaggaatcgc<br>acagaagatcacccagacacagcccggcatgtttgtgcaggagaaggaggccgtgaccctg<br>gattgcacctacgacacatctgatcccagctacggcctgttctggtataagcagccttctagcgg<br>cgagatgatctttctgatctaccagggcagctatgaccagcagaacgccaccgagggcagata<br>ctctctgaatttccagaaggccaggaagagcgccaacctggtcatcagcgcctcccagctggg<br>cgattccgccatgtatttctgtgccatgagaggcgcctcacagggcggctctgagaagctggtg<br>tttggcaagggcaccaagctgacagtgaaccctaatattcagaatccc |
|  | Beta (TRBV5-1*01) | SEQ ID NO: 32<br>atggcgtcccgactgctgtgctgggtcctgctgtgcctgctgggggctgggcctgtcaaagct<br>ggcgtcactcagactccacgatacctgatcaagaccagggccagcaggtgacactgtcttgc<br>agcccaatctccggccaccgctccgtgtcttggtaccagcagacccctggccagggcctcca<br>gttcctgtttgagtatttctctgagacacagcggaacaagggcaatttccccggccggtttagcg<br>gcagacagtttagcaactccaggtctgagatgaatgtgagcaccctggagctgggcgactccg<br>ccctgtacctgtgcgccagctccctgacttctggcgggtttgatgagcagttctttgggcctggc<br>actcggctgaccgtcctg |

In an embodiment of the invention, the nucleic acid comprises a codon-optimized nucleotide sequence encoding any of the TCRs, polypeptides, or proteins described herein. Without being bound to any particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

about 94%, about 95%, about 96%, about 97%, about 98%, or about 99% identical to any of the nucleic acids described herein. In this regard, the nucleic acid may consist essentially of any of the nucleotide sequences described herein.

The nucleic acids of the invention can be incorporated into a recombinant expression vector. In this regard, the invention provides a recombinant expression vector comprising any of the nucleic acids of the invention. In an embodiment of the invention, the recombinant expression vector comprises a nucleotide sequence encoding the α chain, the β chain, and linker peptide.

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotide, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech) Examples of animal expression vectors include pEUK-Cl, pMAM and pMAMneo (Clontech). Preferably, the recombinant expression vector is a viral vector, e.g., a retroviral vector. In an especially preferred embodiment, the recombinant expression vector is an MSGV1 vector.

The recombinant expression vectors of the invention can be prepared using standard recombinant DNA techniques described in, for example, Green and Sambrook et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein, or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, nitroreductase, and the inducible caspase 9 gene system.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α $E.\ coli$ cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5a cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD4^+$ T cells, $CD8^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods*, 128:189-201 (1990). In an embodiment, expansion of the numbers of T cells is carried out by culturing the T cells with OKT3 antibody, IL-2, and feeder PBMC (e.g., irradiated allogeneic PBMC).

The inventive TCRs, polypeptides, proteins, nucleic acids, recombinant expression vectors, and host cells (including populations thereof), can be isolated and/or purified. The term "isolated," as used herein, means having been removed from its natural environment. The term "purified," as used herein, means having been increased in purity, wherein "purity" is a relative term, and not to be necessarily construed as absolute purity. For example, the purity can be at least about 50%, can be greater than about 60%, about 70%, about 80%, about 90%, about 95%, or can be about 100%.

The inventive TCRs, polypeptides, proteins, nucleic acids, recombinant expression vectors, and host cells (including populations thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, nucleic acids, expression vectors, and host cells (including populations thereof), described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Methods for preparing administrable compositions are known or apparent to those skilled in the art and are described in more detail in, for example, *Remington: The Science and Practice of Pharmacy*, 22$^{nd}$. Ed., Pharmaceutical Press (2012). It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell (or population thereof) expressing the inventive TCR, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen (e.g., mutated RAS), or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which each is given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the cancer being treated. In an embodiment in which the inventive TCR material is a population of cells, the number of cells administered per infusion may vary, e.g., from about $1\times10^6$ to about $1\times10^{12}$ cells or more. In certain embodiments, fewer than $1\times10^6$ cells may be administered.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a chemotherapeutic agent. The practice of conjugating compounds to a chemotherapeutic agent is known in the art. One of ordinary skill in the art recognizes that sites on the inventive TCR materials, which are not necessary for the function of the inventive TCR materials, are suitable sites for attaching a bridge and/or a chemotherapeutic agent, provided that the bridge and/or chemotherapeutic agent, once attached to the inventive TCR materials, do(es) not interfere with the function of the inventive TCR materials, i.e., the ability to bind to mutated RAS or to detect, treat, or prevent cancer.

It is contemplated that the inventive pharmaceutical compositions, TCRs, polypeptides, proteins, nucleic acids, recombinant expression vectors, host cells, and populations of cells can be used in methods of treating or preventing cancer. Without being bound to a particular theory, the inventive TCRs are believed to bind specifically to mutated RAS, such that the TCR (or related inventive polypeptide or protein), when expressed by a cell, is able to mediate an immune response against a target cell expressing mutated RAS. In this regard, the invention provides a method of treating or preventing cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the mammal.

An embodiment of the invention provides any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, for use in the treatment or prevention of cancer in a mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof. Alternatively or additionally, "prevention" may encompass preventing or delaying the recurrence of cancer, or a symptom or condition thereof.

Also provided is a method of detecting the presence of cancer in a mammal. The method comprises (i) contacting a sample comprising one or more cells from the mammal with any of the inventive TCRs, polypeptides, proteins, nucleic acids, recombinant expression vectors, host cells, populations of cells, or pharmaceutical compositions described herein, thereby forming a complex, and (ii) detecting the complex, wherein detection of the complex is indicative of the presence of cancer in the mammal.

With respect to the inventive method of detecting cancer in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive method of detecting cancer, the contacting can take place in vitro or in vivo with respect to the mammal. Preferably, the contacting is in vitro.

Also, detection of the complex can occur through any number of ways known in the art. For instance, the inventive TCRs, polypeptides, proteins, nucleic acids, recombinant expression vectors, host cells, or populations of cells, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, colorectal cancer, endometrial cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is pancreatic, colorectal, lung, endometrial, ovarian, or prostate cancer. Preferably, the lung cancer is lung adenocarcinoma, the ovarian cancer is epithelial ovarian cancer, and the pancreatic cancer is pancreatic adenocarcinoma. In an embodiment of the invention, the cancer expresses a mutated human RAS amino acid sequence, wherein the mutated human RAS amino acid sequence is a mutated human KRAS, a mutated human HRAS, or a mutated human NRAS amino acid sequence. The mutated human KRAS, mutated human HRAS, and mutated human NRAS expressed by the cancer may be as described herein with respect to other aspects of the invention.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

Example 1

This example demonstrates the isolation of a TCR having antigenic specificity for human KRAS with the G12V mutation, wherein the mutated KRAS is presented by an HLA-A*11:01 molecule.

The TCR was identified and isolated from an endometrial cancer patient's peripheral blood following in-vitro sensitization (IVS). The patient's cancer cells were found to be expressing the KRAS G12V mutation. Briefly, autologous DCs were pulsed with a mutated peptide (MTEYKLVVVGAVGVGKSALTIQLI) (SEQ ID NO: 26) and co-cultured for 10 days with CD8 T cells sorted from the patient's peripheral blood.

Figure 1B:
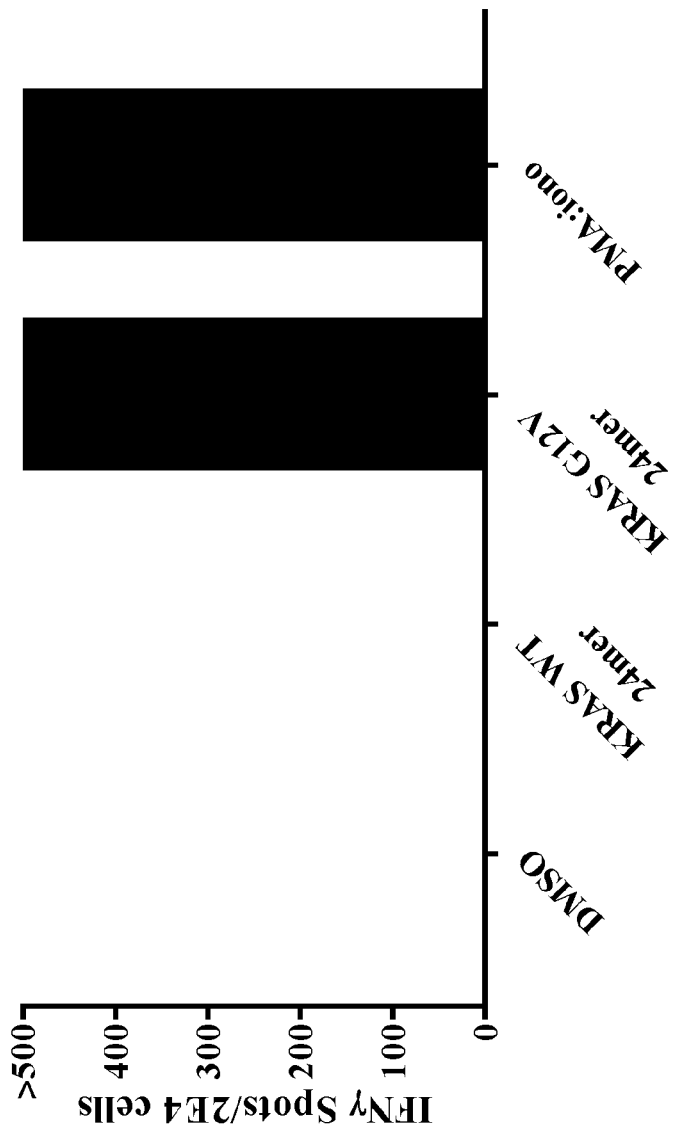
FIG. 1B is a graph showing the number of IFN-γ spots per $2 \times 10^4$ cells following co-culture of T cells with autologous DCs pulsed with DMSO, the KRAS WT 24-mer peptide or the KRAS G12V 24-mer peptide. T cells cultured with PMA: ionomycin and T cells cultured with DCs pulsed with DMSO served as controls.

Next, the reactivity of the T cells was tested against autologous DCs pulsed with a 24-mer peptide encompassing the KRAS G12V mutation (MTEYKLVVVGAVGVGKSALTIQLI) (SEQ ID NO: 26) or the corresponding WT peptide (MTEYKLVVVGAGGVGKSALTIQLI) (SEQ ID NO: 27). The peptides are resuspended in DMSO. T cells cultured with DCs pulsed with DMSO was used as a negative control. T cell reactivity was measured based on CD137 expression and IFN-γ production as measured by ELISPOT assay. Reactive T cells were then sorted based on CD137 expression, the numbers of sorted T cells were expanded, and the sorted, expanded numbers of cells were tested again as described in this Example. The results are shown in FIGS. 1A and 1B. As shown in FIGS. 1A and 1B, the T cells upregulated CD137 expression (FIG. 1A) and increased IFN-γ production (FIG. 1B) only after co-culture with the DC pulsed with the KRAS G12V peptide.

Figure 2:
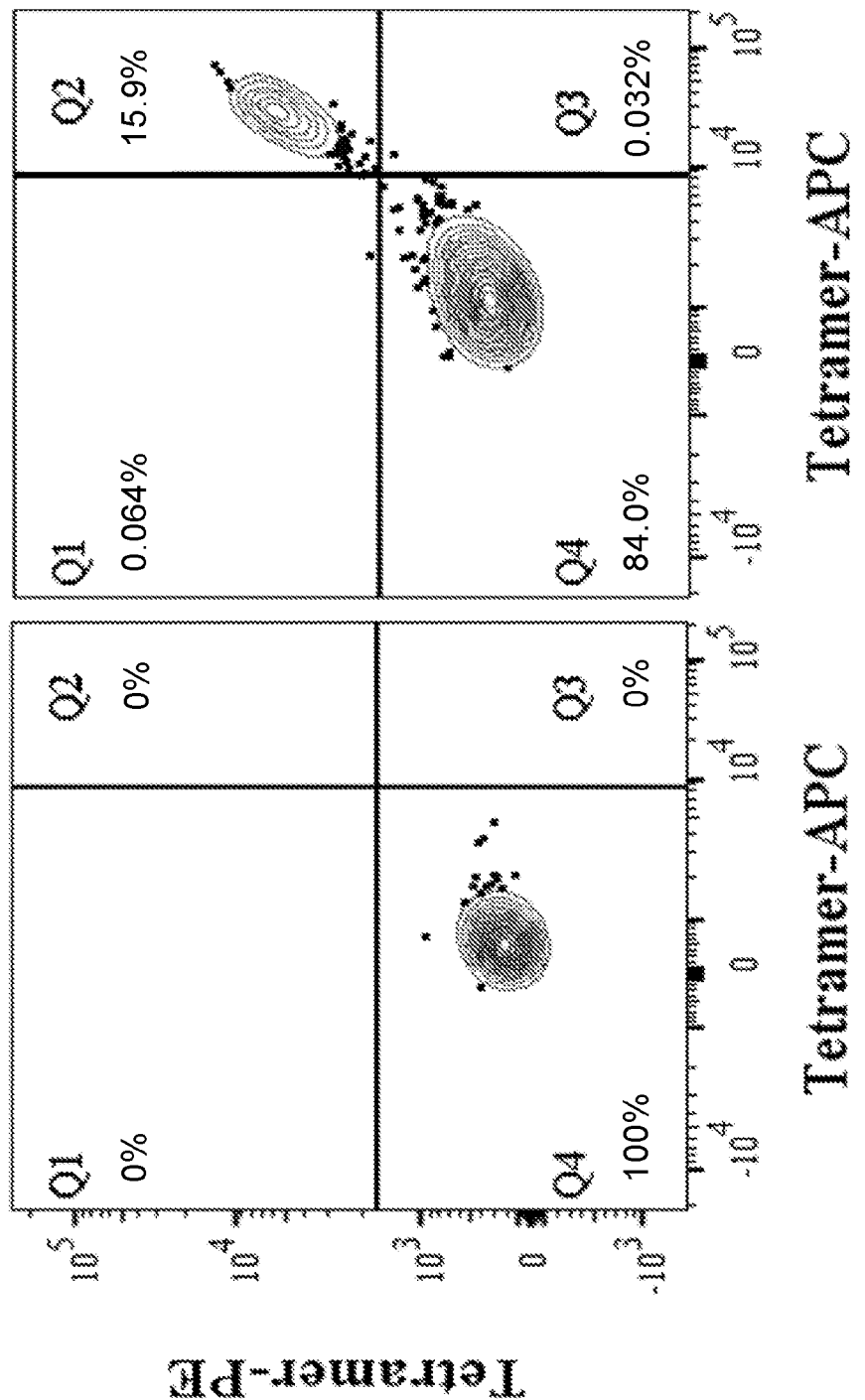
FIG. 2 shows graphs depicting experimental data (dot plots) illustrating the percentage of CD8+ peripheral blood cells, which already underwent IVS with the KRAS G12V 24-mer peptide, which bound to KRAS G12V tetramer-allophycocyanin (APC) or KRAS G12V tetramer-phycoerythrin (PE) (right plot). The left plot shows T cells which had been modified to express a TCR which recognized a KRAS G12D 10-mer in the context of HLA-A*11:01, which bound to KRAS G12V tetramer-APC or KRAS G12V tetramer-PE.

Since the patient was HLA-A*11:01 positive, the KRAS G12V 9-mer and 10-mer peptides were predicted to bind to this allele with high affinity. Therefore, tetramer staining technology was utilized to test whether the T cells were reactive against KRAS$^{G12V}$ in the context of HLA-A*11:01. Peripheral blood CD8+ T cells, which had undergone IVS with the KRAS G12V 24-mer peptide, were stained with the tetramer (9-mer VVGAVGVGK (SEQ ID NO: 29) or 10-mer VVVGAVGVGK (SEQ ID NO: 30)). PE and APC both are fluorophores. The tetramer was conjugated to one of these fluorophores or the other. Staining the cells with both tetramers increases the confidence of the specificity. The results are shown in FIG. 2 (right plot). T cells modified to express a TCR which recognized the KRAS G12D 10-mer in the context of HLA-A*11:01 were used as negative control. The results for the negative control are shown in FIG. 2 (left plot). As shown in FIG. 2, CD8 T cells, which had undergone IVS with the KRAS G12V 24-mer peptide, stained with the KRAS$^{SG12V}$-HLA-A*11:01 tetramer, while the negative control T cells did not.

Sequencing the tetramer-sorted cells using a single cell sequencing method revealed one beta chain and one alpha chain (Table 6). The nucleotide sequences of the TCR alpha and beta chain variable regions were SEQ ID NO: 31 and 32, respectively.

Example 2

This example demonstrates the preparation of an expression cassette encoding the TCR of Example 1 with a cysteine-substituted, LVL-modified murine constant region and the cloning of the expression cassette into a retroviral vector.

The TCR of Example 1 was cloned into a MSGV1-retroviral vector. A nucleic acid sequence encoding the isolated G12V-reactive TCR of Example 1 (comprising the nucleotide sequences of SEQ ID NO: 31 and SEQ ID NO: 32) and including a cysteine substituted, LVL-modified murine constant region was cloned into the retroviral vector. The α chain murine constant region comprised the amino acid sequence of SEQ ID NO: 17 wherein X at position 48 is Cys, X at position 112 is Leu, X at position 114 is Ile, and X at position 115 is Val. The β chain constant region comprised the amino acid sequence of SEQ ID NO: 18, wherein X at position 57 is Cys. A P2A linker comprising the amino acid sequence of SEQ ID NO: 25 (Wargo et al., *Cancer Immunol. Immunother.*, 58(3): 383-94 (2009)) was positioned between the α chain constant region and the β chain variable region. From the 5' to the 3' end, the retroviral vector included a nucleotide sequence encoding the TCR β chain variable region, followed by the modified β chain murine constant region, followed by the P2A linker sequence, followed by the TCR α chain variable region, followed by the modified α chain murine constant region.

Example 3

This example demonstrates that peripheral blood allogeneic T cells transduced with the TCR of Example 2 specifically recognize human KRAS with the G12V mutation, wherein the mutated KRAS is presented by an HLA-A*11:01 molecule.

Figure 3:
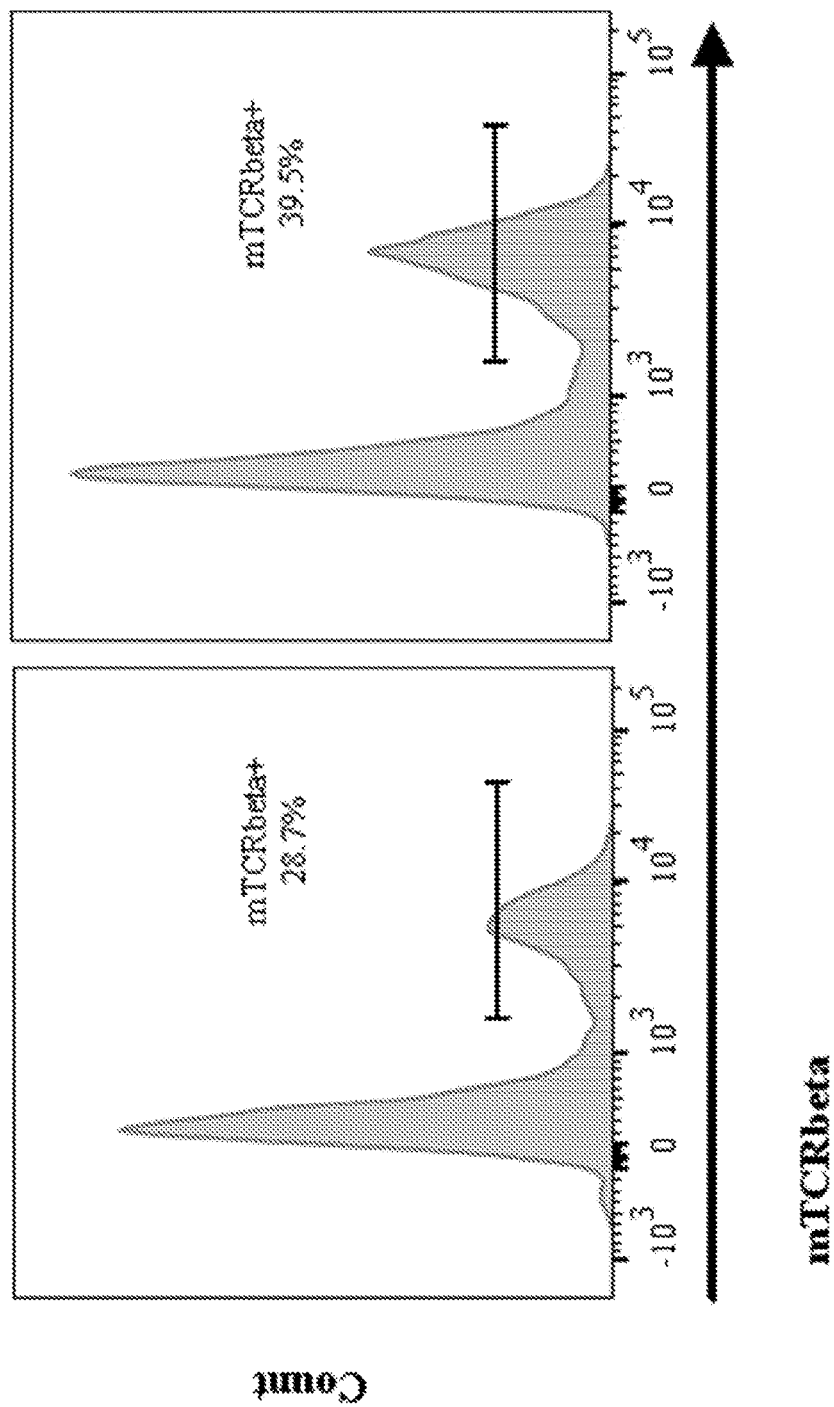
FIG. 3 depicts graphs showing expression of the TCR on the surface of allogenic T cells from first and second donors (left and right panels, respectively) transduced with the TCR of Example 2 as measured by staining for murine TCR beta chain constant region (mTCR beta) expression by flow cytometry. The numbers in the boxes indicate the percentages of cells that were positive for mTCRbeta expression.

Retrovirus encoding the TCR of Example 2 was made and used to transduce peripheral blood allogeneic T cells from two donors (methods as described in Tran et al., N. *Engl. J. Med.*, 375: 2255-2262 (2016)). Expression of the TCR on the surface of the cells was measured by flow cytometry. The results are shown in FIG. 3. As shown in FIG. 3, murine TCR beta chain constant region (mTCRbeta) expression was detected on the surface of the cells.

Figure 4:
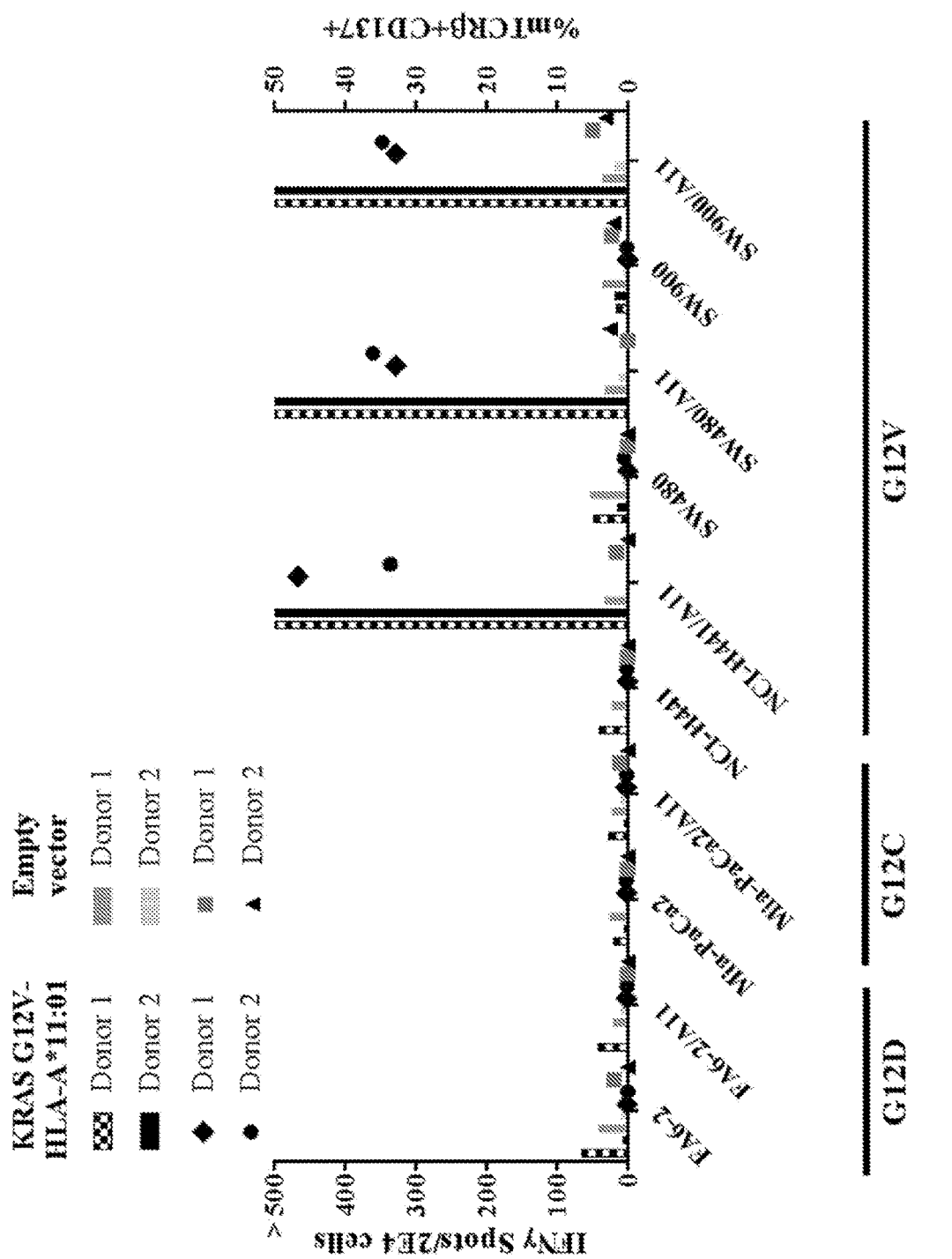
FIG. 4 is a graph showing IFN-γ production as measured by ELISPOT assay (IFN-γ spots per 2E4 cells) and 4-1BB expression (% mTCRβ+CD137+) by T cells from two different donors (Donor 1 and Donor 2) transduced with the TCR of Example 2 after overnight co-culture with cancer cells lines expressing different $KRAS^{G12}$ mutations. Each target cancer cell line was untransduced or transduced with HLA-A*11:01. ">" indicates greater than 500 spots.

The allogeneic cells transduced with the TCR of Example 2 were tested for reactivity against target cancer cell lines expressing KRAS G12D, KRAS G12C, or KRAS G12V. The target cancer cell lines were positive or negative for HLA-A11 expression, as shown in FIG. 4. Reactivity was measured by IFN-γ production (ELISPOT) and CD137 upregulation (flow cytometry). The results are shown in FIG. 4. As shown in FIG. 4, the transduced cells were found to be specifically reactive against cancer cell lines expressing KRAS$^{G12V}$ and HLA-A*11:01.

Example 4

This example demonstrates that the TCR of Example 2 specifically recognizes each of the KRAS G12V 9-mer

TABLE 6

| TCR ID | TCR chain | Amino acid sequence (complementarity determining regions are underlined) |
|---|---|---|
| KRAS$^{G12V}$-HLA-A*11:01 | Alpha (TRAV14/DV4*02) | MSLSSLLKVVTASLWLGPGIAQKITQTQPGMFVQEKEAVTLDCTYDT<u>SDPSYGLFWYKQPSSGEMIFLIY</u>QGSYDQQ<u>NATEGRYSLNFQKARK</u>SANLVISASQLGDSAMYF<u>CAMRGASQGGSEKLVF</u>GKGTKLTVNP (SEQ ID NO: 7) |
|  | Beta (TRBV5-1*01) | MGSRLLCWVLLCLLGAGPVKAGVTQTPRYLIKTRGQQVILSCSPI<u>SG</u><u>HRS</u>VSWYQQTPGQGLQFLFE<u>YFSETQ</u>RNKGNFPGRFSGRQFSNSRSEMNVSTLELGDSALYLC<u>ASSLTSGGFDEQFF</u>GPGTRLTVL (SEQ ID NO: 8) | peptide VVGAVGVGK (SEQ ID NO: 29) and the KRAS G12V 10-mer peptide KRAS G12V 10-mer peptide VVVGAVGVGK (SEQ ID NO: 30).

Figure 5A:
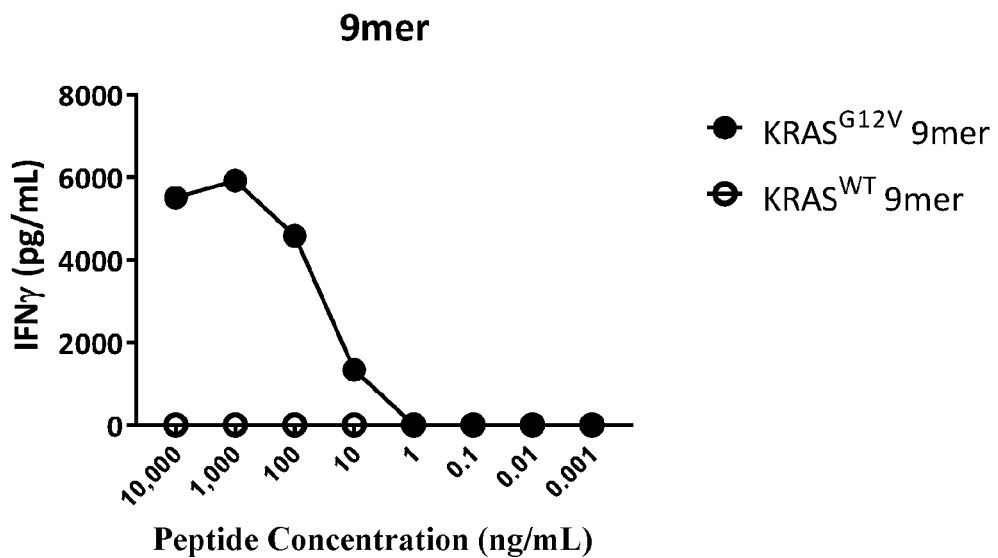
FIG. 5A is a graph showing the concentration (pg/mL) of IFN-γ secreted following co-culture of T cells transduced with the TCR of Example 2 with target cells pulsed with the indicated concentrations (ng/mL) of KRAS G12V 9-mer peptide (closed circles) or KRAS WT 9-mer peptide (open circles).
Figure 5B:
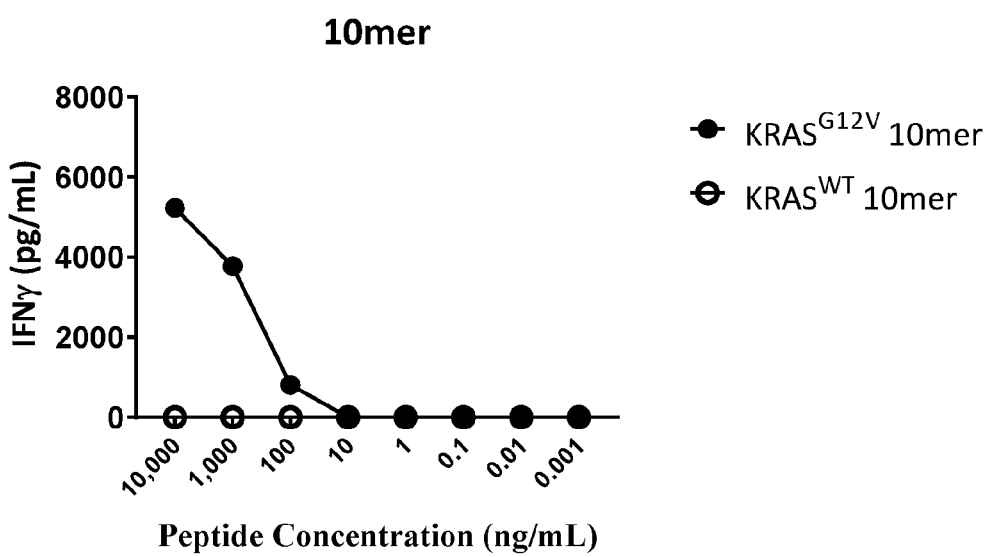
FIG. 5B is a graph showing the concentration (pg/mL) of IFN-γ secreted following co-culture of T cells transduced with the TCR of Example 2 with target cells pulsed with the indicated concentrations (ng/mL) of KRAS G12V 10-mer peptide (closed circles) or KRAS WT 10-mer peptide (open circles).

Allogeneic T cells were transduced with the TCR of Example 2 as described in Example 3. COS7/A11 target cells were pulsed with various concentrations of KRAS G12V 9-mer peptide VVGAVGVGK (SEQ ID NO: 29), KRAS G12V 10-mer peptide VVVGAVGVGK (SEQ ID NO: 30), KRAS WT 9-mer peptide VVGAGGVGK (SEQ ID NO: 33), or KRAS WT 10-mer peptide VVVGAGGVGK (SEQ ID NO: 34). The transduced T cells were co-cultured with the pulsed target cells. IFN-γ secretion was measured. The results are shown in FIG. 5A (9-mers) and FIG. 5B (10-mers). As shown in FIGS. 5A-5B, the TCR specifically recognized each of the KRAS G12V 9-mer peptide and the KRAS G12V 10-mer peptide.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified nucleic acid comprising a nucleotide sequence encoding a T-cell receptor (TCR) comprising the amino acid sequences of (i) SEQ ID NOs: 1-3, (ii) SEQ ID NOs: 4-6, or (iii) SEQ ID NOs: 1-6.

2. The nucleic acid according to claim 1, wherein the TCR comprises a human variable region.

3. The nucleic acid according to claim 1, wherein the TCR comprises:
   (i) the amino acid sequence of SEQ ID NO: 7,
   (ii) an amino acid sequence at least 99% identical to the amino acid sequence of SEQ ID NO: 8, or
   (iii) both the amino acid sequence of SEQ ID NO: 7 and an amino acid sequence at least 99% identical to the amino acid sequence of SEQ ID NO: 8.

4. The nucleic acid according to claim 1, wherein the TCR further comprises:
   (a) an α chain constant region comprising an amino acid sequence at least 99% identical to the amino acid sequence of SEQ ID NO: 17, wherein:
      (i) X at position 48 of SEQ ID NO: 17 is Thr or Cys;
      (ii) X at position 112 of SEQ ID NO: 17 is Ser, Ala, Val, Leu, Ile, Pro, Phe, Met, or Trp;
      (iii) X at position 114 of SEQ ID NO: 17 is Met, Ala, Val, Leu, Ile, Pro, Phe, or Trp; and
      (iv) X at position 115 of SEQ ID NO: 17 is Gly, Ala, Val, Leu, Ile, Pro, Phe, Met, or Trp;
   (b) a β chain constant region comprising the amino acid sequence of SEQ ID NO: 18, wherein X at position 57 of SEQ ID NO: 18 is Ser or Cys; or
   (c) both (a) and (b).

5. The nucleic acid according to claim 1, wherein the TCR comprises:
   (a) an α chain comprising an amino acid sequence at least 99% identical to the amino acid sequence of SEQ ID NO: 21, wherein:
      (i) X at position 185 of SEQ ID NO: 21 is Thr or Cys;
      (ii) X at position 249 of SEQ ID NO: 21 is Ser, Ala, Val, Leu, Ile, Pro, Phe, Met, or Trp;
      (iii) X at position 251 of SEQ ID NO: 21 is Met, Ala, Val, Leu, Ile, Pro, Phe, or Trp; and (iv) X at position 252 of SEQ ID NO: 21 is Gly, Ala, Val, Leu, Ile, Pro, Phe, Met, or Trp;
(b) a β chain comprising an amino acid sequence at least 99% identical to the amino acid sequence of SEQ ID NO: 22, wherein X at position 190 of SEQ ID NO: 22 is Ser or Cys; or
(c) both (a) and (b).

6. The nucleic acid according to claim 1, wherein the TCR has antigenic specificity for a mutated human RAS amino acid sequence presented by a human leukocyte antigen (HLA) Class I molecule, and
wherein the mutated human RAS amino acid sequence is a mutated human Kirsten rat sarcoma viral oncogene homolog (KRAS), a mutated human Harvey rat sarcoma viral oncogene homolog (LIRAS), or a mutated human Neuroblastoma rat sarcoma viral oncogene homolog (NRAS) amino acid sequence.

7. The nucleic acid according to claim 6, wherein the amino acid sequence of the mutated human RAS amino acid sequence comprises or consists of SEQ ID NOs: 29 or 30.

8. The nucleic acid according to claim 6, wherein the HLA Class I molecule is an HLA-A molecule.

9. The nucleic acid according to claim 6, wherein the HLA Class I molecule is an HLA-A11 molecule.

10. The nucleic acid according to claim 6, wherein the HLA Class I molecule is an HLA-A*11:01 molecule.

11. The nucleic acid according to claim 6, wherein the mutated human RAS amino acid sequence comprises a wild-type human KRAS, a wild-type human HRAS, or a wild-type human NRAS amino acid sequence with a substitution of glycine at position 12, wherein position 12 is defined by reference to the wild-type human KRAS, wild-type human HRAS, or wild-type human NRAS protein, respectively.

12. The nucleic acid according to claim 11, wherein the substitution is a substitution of glycine at position 12 with valine.

13. The nucleic acid according to claim 1, wherein the TCR comprises the amino acid sequence of SEQ ID NO: 7, SEQ ID NO: 8, or both of SEQ ID NOs: 7 and 8.

14. The nucleic acid according to claim 1, wherein the TCR comprises:
(a) an α chain constant region comprising an amino acid sequence at least 99% identical to the amino acid sequence of SEQ ID NO: 17, wherein:
(i) X at position 48 of SEQ ID NO: 17 is Cys;
(ii) X at position 112 of SEQ ID NO: 17 is Leu;
(iii) X at position 114 of SEQ ID NO: 17 is Ile; and
(iv) X at position 115 of SEQ ID NO: 17 is Val;
(b) a β chain constant region comprising the amino acid sequence of SEQ ID NO: 18, wherein X at position 57 of SEQ ID NO: 18 is Cys; or
(c) both (a) and (b).

15. The nucleic acid according to claim 1, wherein the TCR comprises:
(a) an α chain comprising an amino acid sequence at least 99% identical to the amino acid sequence of SEQ ID NO: 21, wherein:
(i) X at position 185 of SEQ ID NO: 21 is Cys;
(ii) X at position 249 of SEQ ID NO: 21 is Leu;
(iii) X at position 251 of SEQ ID NO: 21 is Ile; and
(iv) X at position 252 of SEQ ID NO: 21 is Val;
(b) a β chain comprising an amino acid sequence at least 99% identical to the amino acid sequence of SEQ ID NO: 22, wherein X at position 190 of SEQ ID NO: 22 is Cys; or
(c) both (a) and (b).

16. A recombinant expression vector comprising the nucleic acid according to claim 1.

17. An isolated or purified host cell comprising the recombinant expression vector according to claim 16.

18. An isolated or purified population of cells comprising the host cell according to claim 17.

19. A pharmaceutical composition comprising (a) the population of cells according to claim 18 and (b) a pharmaceutically acceptable carrier.

20. A method of detecting the presence of cancer in a mammal, the method comprising:
(a) contacting a sample comprising cells of the cancer with the host cell according to claim 17, thereby forming a complex; and
(b) detecting the complex,
wherein detection of the complex is indicative of the presence of cancer in the mammal.

21. The method according to claim 20, wherein the cancer expresses a mutated human RAS amino acid sequence, wherein the mutated human RAS amino acid sequence is a mutated human KRAS, a mutated human HRAS, or a mutated human NRAS amino acid sequence.

22. The method according to claim 21, wherein the mutated human RAS amino acid sequence comprises a wild-type human KRAS, a wild-type human HRAS, or a wild-type human NRAS amino acid sequence with a substitution of glycine at position 12, wherein position 12 is defined by reference to the wild-type human KRAS, wild-type human HRAS, or wild-type human NRAS amino acid sequence, respectively.

23. The method according to claim 22, wherein the substitution is a substitution of glycine at position 12 with valine.

24. The method according to claim 21, wherein the mutated human RAS amino acid sequence is a mutated human Kirsten rat sarcoma viral oncogene homolog (KRAS) amino acid sequence.

25. The method according to claim 21, wherein the mutated human RAS amino acid sequence is a mutated human neuroblastoma rat sarcoma viral oncogene homolog (NRAS) amino acid sequence.

26. The method according to claim 21, wherein the mutated human RAS amino acid sequence is a mutated human Harvey rat sarcoma viral oncogene homolog (1TRAS) amino acid sequence.

27. The method according to claim 20, wherein the cancer is pancreatic, colorectal, lung, endometrial, ovarian, or prostate cancer.

28. A method of treating cancer in a mammal, comprising administering to the mammal the population of cells according to claim 18 in an amount effective to treat cancer in the mammal.

29. An isolated or purified TCR encoded by the nucleic acid according to claim 1.

30. An isolated or purified nucleic acid comprising a nucleotide sequence encoding a polypeptide, wherein the polypeptide comprises a functional portion of the TCR encoded by the nucleic acid according to claim 1, wherein the functional portion comprises the amino acid sequences of:
(a) all of SEQ ID NOs: 1-3,
(b) all of SEQ ID NOs: 4-6, or
(c) all of SEQ ID NOs: 1-6.

31. The nucleic acid according to claim 30, wherein the functional portion of the TCR comprises:
(i) the amino acid sequence of SEQ ID NO: 7,
(ii) an amino acid sequence at least 99% identical to the amino acid sequence of SEQ ID NO: 8, or (iii) both the amino acid sequence of SEQ ID NO: 7 and an amino acid sequence at least 99% identical to the amino acid sequence of SEQ ID NO: 8.

32. The nucleic acid according to claim 30, wherein the functional portion of the TCR comprises:
   (a) an amino acid sequence at least 99% identical to the amino acid sequence of SEQ ID NO: 17, wherein:
      (i) X at position 48 of SEQ ID NO: 17 is Thr or Cys;
      (ii) X at position 112 of SEQ ID NO: 17 is Ser, Ala, Val, Leu, Ile, Pro, Phe, Met, or Trp;
      (iii) X at position 114 of SEQ ID NO: 17 is Met, Ala, Val, Leu, Ile, Pro, Phe, or Trp; and
      (iv) X at position 115 of SEQ ID NO: 17 is Gly, Ala, Val, Leu, Ile, Pro, Phe, Met, or Trp;
   (b) the amino acid sequence of SEQ ID NO: 18, wherein X at position 57 of SEQ ID NO: 18 is Ser or Cys; or
   (c) both (a) and (b).

33. The nucleic acid according to claim 30, wherein the functional portion of the TCR comprises:
   (a) an amino acid sequence at least 99% identical to the amino acid sequence of SEQ ID NO: 21, wherein:
      (i) X at position 185 of SEQ ID NO: 21 is Thr or Cys;
      (ii) X at position 249 of SEQ ID NO: 21 is Ser, Ala, Val, Leu, Ile, Pro, Phe, Met, or Trp;
      (iii) X at position 251 of SEQ ID NO: 21 is Met, Ala, Val, Leu, Ile, Pro, Phe, or Trp; and
      (iv) X at position 252 of SEQ ID NO: 21 is Gly, Ala, Val, Leu, Ile, Pro, Phe, Met, or Trp;
   (b) an amino acid sequence at least 99% identical to the amino acid sequence of SEQ ID NO: 22, wherein X at position 190 of SEQ ID NO: 22 is Ser or Cys; or
   (c) both (a) and (b).

34. An isolated or purified nucleic acid comprising a nucleotide sequence encoding a protein, wherein the protein comprises the polypeptide according to claim 30.

35. The nucleic acid according to claim 34, wherein the protein comprises a first polypeptide chain comprising the amino acid sequences of SEQ ID NOs: 1-3 and a second polypeptide chain comprising the amino acid sequences of SEQ ID NOs: 4-6.

36. The nucleic acid according to claim 34, wherein the protein comprises a first polypeptide chain comprising the amino acid sequence of SEQ ID NO: 7 and a second polypeptide chain comprising an amino acid sequence at least 99% identical to the amino acid sequence of SEQ ID NO: 8.

37. The nucleic acid according to claim 34, wherein the protein further comprises:
   (a) a first polypeptide chain comprising an amino acid sequence at least 99% identical to the amino acid sequence of SEQ ID NO: 17, wherein:
      (i) X at position 48 of SEQ ID NO: 17 is Thr or Cys;
      (ii) X at position 112 of SEQ ID NO: 17 is Ser, Ala, Val, Leu, Ile, Pro, Phe, Met, or Trp;
      (iii) X at position 114 of SEQ ID NO: 17 is Met, Ala, Val, Leu, Ile, Pro, Phe, or Trp; and
      (iv) X at position 115 of SEQ ID NO: 17 is Gly, Ala, Val, Leu, Ile, Pro, Phe, Met, or Trp;
   (b) a second polypeptide chain comprising the amino acid sequence of SEQ ID NO: 18, wherein X at position 57 of SEQ ID NO: 18 is Ser or Cys; or
   (c) both (a) and (b).

38. The nucleic acid according to claim 34, wherein the protein comprises:
   (a) a first polypeptide chain comprising an amino acid sequence at least 99% identical to the amino acid sequence of SEQ ID NO: 21, wherein:
      (i) X at position 185 of SEQ ID NO: 21 is Thr or Cys;
      (ii) X at position 249 of SEQ ID NO: 21 is Ser, Ala, Val, Leu, Ile, Pro, Phe, Met, or Trp;
      (iii) X at position 251 of SEQ ID NO: 21 is Met, Ala, Val, Leu, Ile, Pro, Phe, or Trp; and
      (iv) X at position 252 of SEQ ID NO: 21 is Gly, Ala, Val, Leu, Ile, Pro, Phe, Met, or Trp;
   (b) a second polypeptide chain comprising an amino acid sequence at least 99% identical to the amino acid sequence of SEQ ID NO: 22, wherein X at position 190 of SEQ ID NO: 22 is Ser or Cys; or
   (c) both (a) and (b).

39. The nucleic acid according to claim 34, wherein the protein comprises a first polypeptide chain comprising the amino acid sequence of SEQ ID NO: 7 and a second polypeptide chain comprising the amino acid sequence of SEQ ID NO: 8.

40. The nucleic acid according to claim 34, wherein the protein comprises:
   (a) an amino acid sequence at least 99% identical to a first polypeptide chain comprising the amino acid sequence of SEQ ID NO: 17, wherein:
      (i) X at position 48 of SEQ ID NO: 17 is Cys;
      (ii) X at position 112 of SEQ ID NO: 17 is Leu;
      (iii) X at position 114 of SEQ ID NO: 17 is Ile; and
      (iv) X at position 115 of SEQ ID NO: 17 is Val;
   (b) a second polypeptide chain comprising the amino acid sequence of SEQ ID NO: 18, wherein X at position 57 of SEQ ID NO: 18 is Cys; or
   (c) both (a) and (b).

41. The nucleic acid according to claim 34, wherein the protein comprises:
   (a) an amino acid sequence at least 99% identical to a first polypeptide chain comprising the amino acid sequence of SEQ ID NO: 21, wherein:
      (i) X at position 185 of SEQ ID NO: 21 is Cys;
      (ii) X at position 249 of SEQ ID NO: 21 is Leu;
      (iii) X at position 251 of SEQ ID NO: 21 is Ile; and
      (iv) X at position 252 of SEQ ID NO: 21 is Val;
   (b) an amino acid sequence at least 99% identical to a second polypeptide chain comprising the amino acid sequence of SEQ ID NO: 22, wherein X at position 190 of SEQ ID NO: 22 is Cys; or
   (c) both (a) and (b).

42. The nucleic acid according to claim 30, wherein the functional portion of the TCR comprises the amino acid sequence of SEQ ID NO: 7, SEQ ID NO: 8, or both of SEQ ID NOs: 7 and 8.

43. The nucleic acid according to claim 30, wherein the functional portion of the TCR comprises:
   (a) an amino acid sequence at least 99% identical to the amino acid sequence of SEQ ID NO: 17, wherein:
      (i) X at position 48 of SEQ ID NO: 17 is Cys;
      (ii) X at position 112 of SEQ ID NO: 17 is Leu;
      (iii) X at position 114 of SEQ ID NO: 17 is Ile; and
      (iv) X at position 115 of SEQ ID NO: 17 is Val;
   (b) the amino acid sequence of SEQ ID NO: 18, wherein X at position 57 of SEQ ID NO: 18 is Cys; or
   (c) both (a) and (b).

44. The nucleic acid according to claim 30, wherein the functional portion of the TCR comprises:
   (a) an amino acid sequence at least 99% identical to the amino acid sequence of SEQ ID NO: 21, wherein:
      (i) X at position 185 of SEQ ID NO: 21 is Cys;
      (ii) X at position 249 of SEQ ID NO: 21 is Leu;
      (iii) X at position 251 of SEQ ID NO: 21 is Ile; and
      (iv) X at position 252 of SEQ ID NO: 21 is Val;

(b) an amino acid sequence at least 99% identical to the amino acid sequence of SEQ ID NO: 22, wherein X at position 190 of SEQ ID NO: 22 is Cys; or
(c) both (a) and (b).

* * * * *

SEQUENCE LISTING

<160> NUMBER OF SEQ ID NOS: 34

<210> SEQ ID NO 1
<211> LENGTH: 7
<212> TYPE: PRT
<213> ORGANISM: Homo sapiens

<400> SEQUENCE: 1

Thr Ser Asp Pro Ser Tyr Gly
1               5

<210> SEQ ID NO 2
<211> LENGTH: 8
<212> TYPE: PRT
<213> ORGANISM: Homo sapiens

<400> SEQUENCE: 2

Gln Gly Ser Tyr Asp Gln Gln Asn
1               5

<210> SEQ ID NO 3
<211> LENGTH: 16
<212> TYPE: PRT
<213> ORGANISM: Homo sapiens

<400> SEQUENCE: 3

Cys Ala Met Arg Gly Ala Ser Gln Gly Gly Ser Glu Lys Leu Val Phe
1               5                   10                  15

<210> SEQ ID NO 4
<211> LENGTH: 5
<212> TYPE: PRT
<213> ORGANISM: Homo sapiens

<400> SEQUENCE: 4

Ser Gly His Arg Ser
1               5

<210> SEQ ID NO 5
<211> LENGTH: 6
<212> TYPE: PRT
<213> ORGANISM: Homo sapiens

<400> SEQUENCE: 5

Tyr Phe Ser Glu Thr Gln
1               5

<210> SEQ ID NO 6
<211> LENGTH: 15
<212> TYPE: PRT
<213> ORGANISM: Homo sapiens

<400> SEQUENCE: 6

Cys Ala Ser Ser Leu Thr Ser Gly Gly Phe Asp Glu Gln Phe Phe
1               5                   10                  15

<210> SEQ ID NO 7
<211> LENGTH: 137
<212> TYPE: PRT
<213> ORGANISM: Homo sapiens

<400> SEQUENCE: 7

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Gly Ala Ser Gln Gly Gly Ser Glu Lys Leu Val Phe Gly
        115                 120                 125

Lys Gly Thr Lys Leu Thr Val Asn Pro
    130                 135

<210> SEQ ID NO 8
<211> LENGTH: 133
<212> TYPE: PRT
<213> ORGANISM: Homo sapiens

<400> SEQUENCE: 8

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
 50                  55                  60

Leu Phe Glu Tyr Phe Ser Glu Thr Gln Arg Asn Lys Gly Asn Phe Pro
 65                  70                  75                  80

Gly Arg Phe Ser Gly Arg Gln Phe Ser Asn Ser Arg Ser Glu Met Asn
                 85                  90                  95

Val Ser Thr Leu Glu Leu Gly Asp Ser Ala Leu Tyr Leu Cys Ala Ser
                100                 105                 110

Ser Leu Thr Ser Gly Gly Phe Asp Glu Gln Phe Phe Gly Pro Gly Thr
            115                 120                 125

Arg Leu Thr Val Leu
    130

<210> SEQ ID NO 9
<211> LENGTH: 189
<212> TYPE: PRT
<213> ORGANISM: Homo sapiens

<400> SEQUENCE: 9

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 10
<211> LENGTH: 188
<212> TYPE: PRT
<213> ORGANISM: Homo sapiens

<400> SEQUENCE: 10

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

```
Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
                180                 185

<210> SEQ ID NO 11
<211> LENGTH: 189
<212> TYPE: PRT
<213> ORGANISM: Homo sapiens

<400> SEQUENCE: 11

Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
                100                 105                 110

Leu Val Gly Asn Lys Cys Asp Leu Ala Ala Arg Thr Val Glu Ser Arg
                115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
                180                 185

<210> SEQ ID NO 12
<211> LENGTH: 189
<212> TYPE: PRT
<213> ORGANISM: Homo sapiens
```

<400> SEQUENCE: 12

Met Thr Glu Tyr Lys Leu Val Val Gly Ala Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Val Pro Met Val
                100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185

<210> SEQ ID NO 13
<211> LENGTH: 189
<212> TYPE: PRT
<213> ORGANISM: Homo sapiens

<400> SEQUENCE: 13

Met Thr Glu Tyr Lys Leu Val Val Gly Ala Val Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Lys
              165                 170                 175

Thr Pro Gly Cys Val Lys Ile Lys Lys Cys Ile Ile Met
            180                 185

<210> SEQ ID NO 14
<211> LENGTH: 188
<212> TYPE: PRT
<213> ORGANISM: Homo sapiens

<400> SEQUENCE: 14

Met Thr Glu Tyr Lys Leu Val Val Val Gly Ala Val Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 15
<211> LENGTH: 189
<212> TYPE: PRT
<213> ORGANISM: Homo sapiens

<400> SEQUENCE: 15

Met Thr Glu Tyr Lys Leu Val Val Val Gly Ala Val Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
            100                 105                 110

```
Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

```
<210> SEQ ID NO 16
<211> LENGTH: 189
<212> TYPE: PRT
<213> ORGANISM: Homo sapiens

<400> SEQUENCE: 16

Met Thr Glu Tyr Lys Leu Val Val Gly Ala Val Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Ile Asp Gly
        35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Val Pro Met Val
            100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185
```

```
<210> SEQ ID NO 17
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (48)..(48)
<223> OTHER INFORMATION: X is Thr or Cys
<220> FEATURE:
<221> NAME/KEY: MISC_FEATURE
<222> LOCATION: (112)..(112)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (114)..(114)
<223> OTHER INFORMATION: X is Met, Ala, Val, Leu, Ile, Pro, Phe, or Trp
```

```
<220> FEATURE:
<221> NAME/KEY: MISC_FEATURE
<222> LOCATION: (115)..(115)
<223> OTHER INFORMATION: X is Gly, Ala, Val, Leu, Ile, Pro, Phe, Met, or
      Trp

<400> SEQUENCE: 17
```

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Xaa
        35                  40                  45

Val Leu Asp Met Lys Ala Met Asp Ser Lys Ser Asn Gly Ala Ile Ala
50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Xaa
            100                 105                 110

Val Xaa Xaa Leu Arg Ile Leu Leu Leu Lys Val Ala Gly Phe Asn Leu
        115                 120                 125

Leu Met Thr Leu Arg Leu Trp Ser Ser
130                 135

```
<210> SEQ ID NO 18
<211> LENGTH: 173
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (57)..(57)
<223> OTHER INFORMATION: X is Ser or Cys

<400> SEQUENCE: 18
```

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Xaa Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 19
<211> LENGTH: 137
<212> TYPE: PRT
<213> ORGANISM: Mus musculus

<400> SEQUENCE: 19

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
                20                  25                  30

Asn Val Pro Lys Thr Met Glu Ser Gly Thr Phe Ile Thr Asp Lys Thr
            35                  40                  45

Val Leu Asp Met Lys Ala Met Asp Ser Lys Ser Asn Gly Ala Ile Ala
        50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135

<210> SEQ ID NO 20
<211> LENGTH: 173
<212> TYPE: PRT
<213> ORGANISM: Mus musculus

<400> SEQUENCE: 20

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
                20                  25                  30

Ala Arg Gly Phe Phe Pro Asp His Val Glu Leu Ser Trp Trp Val Asn
            35                  40                  45

Gly Lys Glu Val His Ser Gly Val Ser Thr Asp Pro Gln Ala Tyr Lys
        50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
        130                 135                 140

-continued

```
Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 21
<211> LENGTH: 274
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (185)..(185)
<223> OTHER INFORMATION: X is Thr or Cys
<220> FEATURE:
<221> NAME/KEY: MISC_FEATURE
<222> LOCATION: (249)..(249)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (251)..(251)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (252)..(252)
<223> OTHER INFORMATION: X is Gly, Ala, Val, Leu, Ile, Pro, Phe, Met, or
      Trp

<400> SEQUENCE: 21

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
                20                  25                  30

Val Gln Glu Lys Glu Ala Val Thr Leu Asp Cys Thr Tyr Asp Thr Ser
            35                  40                  45

Asp Pro Ser Tyr Gly Leu Phe Trp Tyr Lys Gln Pro Ser Ser Gly Glu
        50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Gly Ala Ser Gln Gly Gly Ser Glu Lys Leu Val Phe Gly
        115                 120                 125

Lys Gly Thr Lys Leu Thr Val Asn Pro Asp Ile Gln Asn Pro Glu Pro
    130                 135                 140

Ala Val Tyr Gln Leu Lys Asp Pro Arg Ser Gln Asp Ser Thr Leu Cys
145                 150                 155                 160

Leu Phe Thr Asp Phe Asp Ser Gln Ile Asn Val Pro Lys Thr Met Glu
                165                 170                 175

Ser Gly Thr Phe Ile Thr Asp Lys Xaa Val Leu Asp Met Lys Ala Met
            180                 185                 190

Asp Ser Lys Ser Asn Gly Ala Ile Ala Trp Ser Asn Gln Thr Ser Phe
        195                 200                 205

Thr Cys Gln Asp Ile Phe Lys Glu Thr Asn Ala Thr Tyr Pro Ser Ser
    210                 215                 220

Asp Val Pro Cys Asp Ala Thr Leu Thr Glu Lys Ser Phe Glu Thr Asp
225                 230                 235                 240
```

Met Asn Leu Asn Phe Gln Asn Leu Xaa Val Xaa Xaa Leu Arg Ile Leu
                 245                 250                 255

Leu Leu Lys Val Ala Gly Phe Asn Leu Leu Met Thr Leu Arg Leu Trp
            260                 265                 270

Ser Ser

<210> SEQ ID NO 22
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (190)..(190)
<223> OTHER INFORMATION: X is Ser or Cys

<400> SEQUENCE: 22

Met Gly Ser Arg Leu Leu Cys Trp Val Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
            35                  40                  45

Arg Ser Val Ser Trp Tyr Gln Gln Thr Pro Gly Gln Gly Leu Gln Phe
        50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Leu Thr Ser Gly Gly Phe Asp Glu Gln Phe Phe Gly Pro Gly Thr
        115                 120                 125

Arg Leu Thr Val Leu Glu Asp Leu Arg Asn Val Thr Pro Pro Lys Val
130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Xaa Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

```
Ala Val Leu Val Ser Thr Leu Val Val Met Ala Met Val Lys Arg Lys
            290                 295                 300

Asn Ser
305
```

<210> SEQ ID NO 23
<211> LENGTH: 274
<212> TYPE: PRT
<213> ORGANISM: Artificial Sequence
<220> FEATURE:
<223> OTHER INFORMATION: Synthetic

<400> SEQUENCE: 23

```
Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Gly Ala Ser Gln Gly Gly Ser Glu Lys Leu Val Phe Gly
        115                 120                 125

Lys Gly Thr Lys Leu Thr Val Asn Pro Asp Ile Gln Asn Pro Glu Pro
    130                 135                 140

Ala Val Tyr Gln Leu Lys Asp Pro Arg Ser Gln Asp Ser Thr Leu Cys
145                 150                 155                 160

Leu Phe Thr Asp Phe Asp Ser Gln Ile Asn Val Pro Lys Thr Met Glu
                165                 170                 175

Ser Gly Thr Phe Ile Thr Asp Lys Thr Val Leu Asp Met Lys Ala Met
            180                 185                 190

Asp Ser Lys Ser Asn Gly Ala Ile Ala Trp Ser Asn Gln Thr Ser Phe
        195                 200                 205

Thr Cys Gln Asp Ile Phe Lys Glu Thr Asn Ala Thr Tyr Pro Ser Ser
    210                 215                 220

Asp Val Pro Cys Asp Ala Thr Leu Thr Glu Lys Ser Phe Glu Thr Asp
225                 230                 235                 240

Met Asn Leu Asn Phe Gln Asn Leu Ser Val Met Gly Leu Arg Ile Leu
                245                 250                 255

Leu Leu Lys Val Ala Gly Phe Asn Leu Leu Met Thr Leu Arg Leu Trp
            260                 265                 270

Ser Ser
```

<210> SEQ ID NO 24
<211> LENGTH: 306
<212> TYPE: PRT
<213> ORGANISM: Artificial Sequence
<220> FEATURE:
<223> OTHER INFORMATION: Synthetic

<400> SEQUENCE: 24

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Leu Thr Ser Gly Gly Phe Asp Glu Gln Phe Phe Gly Pro Gly Thr
        115                 120                 125

Arg Leu Thr Val Leu Glu Asp Leu Arg Asn Val Thr Pro Pro Lys Val
130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
290                 295                 300

Asn Ser
305

<210> SEQ ID NO 25
<211> LENGTH: 27
<212> TYPE: PRT
<213> ORGANISM: Artificial Sequence
<220> FEATURE:
<223> OTHER INFORMATION: Synthetic

<400> SEQUENCE: 25

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

```
<210> SEQ ID NO 26
<211> LENGTH: 24
<212> TYPE: PRT
<213> ORGANISM: Homo sapiens

<400> SEQUENCE: 26

Met Thr Glu Tyr Lys Leu Val Val Val Gly Ala Val Gly Val Gly Lys
1               5                   10                  15

Ser Ala Leu Thr Ile Gln Leu Ile
            20

<210> SEQ ID NO 27
<211> LENGTH: 24
<212> TYPE: PRT
<213> ORGANISM: Homo sapiens

<400> SEQUENCE: 27

Met Thr Glu Tyr Lys Leu Val Val Val Gly Ala Gly Gly Val Gly Lys
1               5                   10                  15

Ser Ala Leu Thr Ile Gln Leu Ile
            20

<210> SEQ ID NO 28
<211> LENGTH: 23
<212> TYPE: PRT
<213> ORGANISM: Homo sapiens

<400> SEQUENCE: 28

Thr Glu Tyr Lys Leu Val Val Val Gly Ala Gly Gly Val Gly Lys Ser
1               5                   10                  15

Ala Leu Thr Ile Gln Leu Ile
            20

<210> SEQ ID NO 29
<211> LENGTH: 9
<212> TYPE: PRT
<213> ORGANISM: Homo sapiens

<400> SEQUENCE: 29

Val Val Gly Ala Val Gly Val Gly Lys
1               5

<210> SEQ ID NO 30
<211> LENGTH: 10
<212> TYPE: PRT
<213> ORGANISM: Homo sapiens

<400> SEQUENCE: 30

Val Val Val Gly Ala Val Gly Val Gly Lys
1               5                   10

<210> SEQ ID NO 31
<211> LENGTH: 426
<212> TYPE: DNA
<213> ORGANISM: Homo sapiens

<400> SEQUENCE: 31
atgcatctga gctccctgct gaaggtggtg acagccagcc tgtggctggg accaggaatc      60
gcacagaaga tcacccagac acagcccggc atgtttgtgc aggagaagga ggccgtgacc     120
ctggattgca cctacgacac atctgatccc agctacggcc tgttctggta taagcagcct     180
tctagcggcg agatgatctt tctgatctac cagggcagct atgaccagca gaacgccacc     240
```

```
gagggcagat actctctgaa tttccagaag gccaggaaga gcgccaacct ggtcatcagc      300
gcctcccagc tgggcgattc cgccatgtat ttctgtgcca tgagaggcgc ctcacagggc      360
ggctctgaga agctggtgtt tggcaagggc accaagctga cagtgaaccc taatattcag      420
aatccc                                                                  426

<210> SEQ ID NO 32
<211> LENGTH: 399
<212> TYPE: DNA
<213> ORGANISM: Homo sapiens

<400> SEQUENCE: 32
atggcgtccc gactgctgtg ctgggtcctg ctgtgcctgc tgggggctgg gcctgtcaaa       60
gctggcgtca ctcagactcc acgatacctg atcaagacca ggggccagca ggtgacactg      120
tcttgcagcc caatctccgg ccaccgctcc gtgtcttggt accagcagac ccctggccag      180
ggcctccagt tcctgtttga gtatttctct gagacacagc ggaacaaggg caatttcccc      240
ggccggttta gcggcagaca gtttagcaac tccaggtctg agatgaatgt gagcaccctg      300
gagctgggcg actccgccct gtacctgtgc gccagctccc tgacttctgg cgggtttgat      360
gagcagttct ttgggcctgg cactcggctg accgtcctg                             399

<210> SEQ ID NO 33
<211> LENGTH: 9
<212> TYPE: PRT
<213> ORGANISM: Homo sapiens

<400> SEQUENCE: 33

Val Val Gly Ala Gly Gly Val Gly Lys
1               5

<210> SEQ ID NO 34
<211> LENGTH: 10
<212> TYPE: PRT
<213> ORGANISM: Homo sapiens

<400> SEQUENCE: 34

Val Val Val Gly Ala Gly Gly Val Gly Lys
1               5                   10
```